United States Patent [19]

Myers et al.

[11] Patent Number: 5,252,560
[45] Date of Patent: Oct. 12, 1993

[54] CYCLIC IMIDE DERIVATIVES, COMPOSITIONS AND USE

[75] Inventors: Peter L. Myers, Chapel Hill; Andrew B. McElroy, Durham, both of N.C.; Michael Gregson, Greenford, Great Britain; Peter J. Brown, Chapel Hill, N.C.; Howard G. Davies, Greenford, Great Britain; David H. Drewry, Durham; Michael A. Foley, Chapel Hill, both of N.C.

[73] Assignee: Glaxo Inc., Research Triangle Park, N.C.

[21] Appl. No.: 905,933

[22] Filed: Jun. 29, 1992

[30] Foreign Application Priority Data

Jun. 27, 1991 [GB] United Kingdom ............... 9113844.6
Jun. 27, 1991 [GB] United Kingdom ............... 9113930.3
Apr. 30, 1992 [GB] United Kingdom ............... 9209402.8
May 14, 1992 [GB] United Kingdom ............... 9210343.1

[51] Int. Cl.$^5$ ............... A61K 37/02; C07D 209/66; C07D 413/12
[52] U.S. Cl. ............... 514/19; 544/142; 548/433; 548/451; 548/477
[58] Field of Search ............... 544/142; 548/451, 477, 548/433; 514/232.8, 411, 19

[56] References Cited

U.S. PATENT DOCUMENTS 4,511,504 4/1985 McCullagh et al. ......... 260/112.5 R

FOREIGN PATENT DOCUMENTS

| 53158/90 | 10/1990 | Australia. |
| 767777 | 5/1971 | Belgium. |
| 0236872A2 | 9/1987 | European Pat. Off.. |
| 0276436A1 | 8/1988 | European Pat. Off.. |
| 0320118A2 | 6/1989 | European Pat. Off.. |
| 0369391A2 | 5/1990 | European Pat. Off.. |
| 0489577A1 | 6/1992 | European Pat. Off.. |
| 0489579A1 | 6/1992 | European Pat. Off.. |
| WO91/02716 | 3/1991 | PCT Int'l Appl.. |
| WO91/15506 | 10/1991 | PCT Int'l Appl.. |
| WO91/15507 | 10/1991 | PCT Int'l Appl.. |
| WO92/09565 | 6/1992 | PCT Int'l Appl.. |

OTHER PUBLICATIONS

L. A. Liotta, et al, "Metastatic potential correlates with enzymatic degradation of basement membrane collagen", *Nature*, 284, 67–68 (1980).

Chantry, et al, "Metalloendoprotease Cleavage of 18.2- and 14.1-Kilodalton Basic Proteins Dissociating from Rodent Myelin Membranes Generates 10.0- and 5.9-Kilodalton C-Terminal Fragments", *J. Neurochem*, 50, No. 3, 688–694 (1988).

Gravallese, et al, "In Situ Hybridization Studies Of Stromelysim and Collagen Messenger RNA Expression in Rheumatoid Synovium", *Arthritis and Rheumatism*, 34, No. 9, 1076–1084 (1991).

Wooley, et al, "Collagenase at Sites of Cartilage Erosion in the Rheumatoid Joint" *Arthritis and Rheumatism*, 20, No. 6, 1231–1239 (1977).

*Primary Examiner*—Robert W. Ramsuer
*Attorney, Agent, or Firm*—David J. Levy

[57] ABSTRACT

Compounds are described of the formula

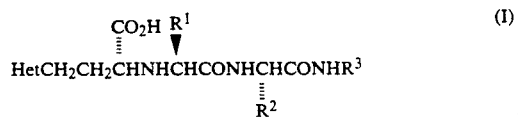

wherein:

$R^1$ is $C_{3-6}$alkyl or $C_{1-3}$alkylthio$C_{1-3}$alkyl;

$R^2$ is an optionally substituted $C_{1-6}$alkyl or $C_{1-6}$alkoxy group, aryl, heteroaryl, aryl$C_{1-4}$alkyl, heteroaryl$C_{1-4}$alkyl or a side-chain of a natural α-amino acid;

$R^3$ is hydrogen, $C_{1-6}$alkyl, $CHR^4COR^5$ (where $R^4$ is a side-chain of a natural α-amino acid and $R^5$ is hydroxyl, $C_{1-6}$alkoxy or $NHR^6$ where $R^6$ represents a hydrogen atom or a $C_{1-6}$alkyl group) or a group $(CH_2)_nX$ (where n is 1 to 6 and X is hydroxyl, $C_{1-4}$alkoxy, heteroaryl or a group $NR^7R^8$ where $R^7$ and $R^8$ are each hydrogen or $C_{1-6}$alkyl or the group $NR^7R^8$ forms a 5 to 7 membered cyclic amine); and Het is an optionally substituted cyclic imide where the cyclic imide ring system has the formula (i), (ii) or (iii)

(Abstract continued on next page.)

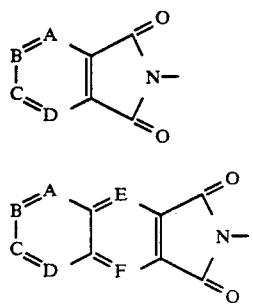 (i)

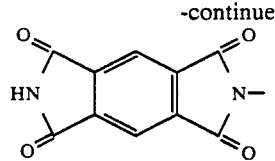 (iii)

(ii)

in which A, B, C and D are each CH or 1 or 2 of A, B, C and D represents N and the others represent CH, and E and F may each independently represent CH or N; and physiologically acceptable salts and solvates thereof.

These compounds inhibit metalloproteases involved in tissue degradation. Compounds of the invention may be formulated for use in a variety of conditions involving tissue degradation including arthropathy, dermatological conditions, bone resorption, inflammatory diseases, tumour invasion and multiple sclerosis and related diseases involving myelin degradation, and in the promotion of wound healing.

11 Claims, No Drawings

CYCLIC IMIDE DERIVATIVES, COMPOSITIONS AND USE

The present invention relates to therapeutically active cyclic imides, processes for the manufacture of said compounds, pharmaceutical formulations containing said compounds and the use of said compounds in chemotherapy. In particular we have found a novel group of cyclic imides which act as inhibitors of metalloproteases involved in tissue degradation.

A number of small peptide-like compounds which inhibit metalloproteases have been described previously. Perhaps the most notable of these are those relating to the angiotensin converting enzyme (ACE) where such agents act to block the conversion of the decapeptide angiotensin I to angiotensin II, a potent pressor substance. Compounds structurally similar to the ACE inhibitors have been developed by Searle as inhibitors of collagenase as in U.S. Pat. No. 4,115,504. A major problem associated with such compounds however is their general lack of intrinsic potency.

Thiol based derivatives have been suggested as collagenase inhibitors as have hydroxamic acid based derivatives (cf Published International Application WO91/02716). Although such compounds have improved intrinsic potency they exhibit poor pharmacokinetics.

Recently, Hoffman-La Roche reported a series of phosphinic acid derivatives as inhibitors of collagenase as in Published European Application EP-A-0276436.

It would be desirable to improve on the potency and/or pharmacokinetics of known collagenase inhibitors and stromelysin inhibitors. To this end we have developed a novel series of compounds which are described hereinafter.

Thus, according to a first aspect of the invention, there is provided a compound of general formula (I)

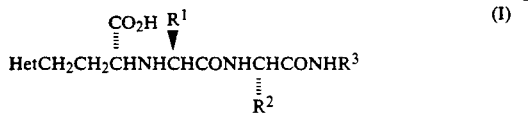

wherein:
$R^1$ is $C_{3-6}$alkyl or $C_{1-3}$alkylthio$C_{1-3}$alkyl;
$R^2$ is an optionally substituted $C_{1-6}$alkyl or $C_{1-6}$alkoxy group, aryl, heteroaryl, aryl$C_{1-4}$alkyl, heteroaryl$C_{1-4}$alkyl or a side-chain of a natural α-amino acid;
$R^3$ is hydrogen, $C_{1-6}$alkyl, $CHR^4COR^5$ (where $R^4$ is a side-chain of a natural α-amino acid and $R^5$ is hydroxyl, $C_{1-6}$alkoxy or $NHR^6$ where $R^6$ represents a hydrogen atom or a $C_{1-6}$alkyl group) or a group $(CH_2)_nX$ (where n is 1 to 6 and X is hydroxyl, $C_{1-4}$alkoxy, heteroaryl or a group $NR^7R^8$ where $R^7$ and $R^8$ are each hydrogen or $C_{1-6}$alkyl or the group $NR^7R^8$ forms a 5 to 7 membered cyclic amine); and
Het is an optionally substituted cyclic imide where the cyclic imide ring system has the formula (i), (ii) or (iii)

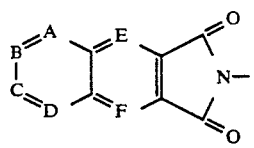

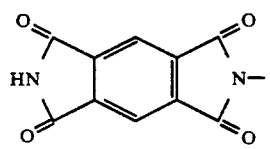

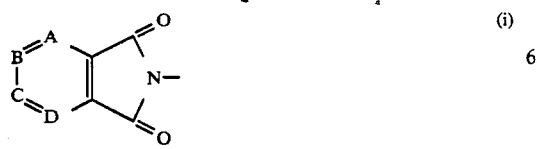

in which A, B, C and D are each CH or 1 or 2 of A, B, C and D represents N and the others represent CH, and E and F may each independently represent CH or N; and physiologically acceptable salts and solvates thereof.

Suitable physiologically acceptable salts of the compounds of formula (I) include acid addition salts formed with organic or inorganic acids [for example, hydrochlorides, hydrobromides, sulphates, alkyl- or arylsulphonates (e.g. methanesulphonates or p-toluenesulphonates), phosphates, acetates, citrates, succinates, lactates, tartrates, fumarates and maleates] and inorganic base salts such as alkali metal salts (for example sodium salts). The solvates may, for example, be hydrates.

Other salts which are not physiologically acceptable may be useful in the preparation of compounds of formula (I) and these form a further aspect of the invention.

It is to be understood that the present invention encompasses the individual enantiomer of the compounds represented by formula (I) above as well as wholly or partially racemic mixtures thereof. The present invention also covers the individual enantiomer of the compounds represented by formula (I) above as mixtures with diastereoisomers thereof in which one or more of the three stereocentres is inverted.

As used herein, the term 'alkyl' as a group or part of a group refers to a straight or branched chain alkyl moiety, including for example methyl, ethyl, propyl, isopropyl, n-butyl, s-butyl and t-butyl.

The term 'optionally substituted $C_{1-6}$alkyl or $C_{1-6}$alkoxy' means a $C_{1-6}$alkyl group which may be substituted by $C_{1-6}$alkoxy or $CO_2R^9$ (where $R^9$ is hydrogen or $C_{1-6}$alkyl), or a $C_{1-6}$alkoxy group which may be substituted by $C_{1-3}$alkoxy.

The term 'aryl' as a group or part of an aryl$C_{1-4}$alkyl group refers to an optionally substituted phenyl or naphthyl group, and the term 'heteroaryl' as a group of part of a heteroaryl$C_{1-4}$alkyl group refers to an optionally substituted 5- or 6-membered heterocyclic group containing one or more heteroatoms selected from S, N and O and optionally fused to a benzene ring. The aryl and heteroaryl ring systems referred to above may be substituted by one or more substituents selected from halogen, hydroxyl, $C_{1-3}$alkoxy and $C_{1-3}$alkyl. Examples of suitable heteroaryl ring systems included indole, imidazole, triazole, tetrazole, oxazole, isoxazole, thiazole, oxadiazole, pyridine, pyrimidine, furan, pyrrole, thiofuran, benzimidazole, benzothiazole, benzoxazole, etc.

The term 'halogen' means a fluorine, chlorine, bromine or iodine atom.

The term 'side-chain of a natural α-amino acid' means a characteristic side-chain R of an α-amino acid of the formula H₂NCH(R)COOH which is naturally occurring or a derivative thereof in which any functional group present is protected or any amino group present is acylated or sulphonylated or any carboxyl group present is amidated. Examples of suitable side-chains include the following with the corresponding α-amino acid in parenthesis: hydrogen (glycine), methyl (alanine), isopropyl (valine), isobutyl (leucine), phenyl (phenylglycine), benzyl (phenylalanine), p-hydroxybenzyl (tyrosine), mercaptomethyl (cysteine), hydroxymethyl (serine), 1-hydroxyethyl (threonine), 2-methylthioethyl (methionine), carboxymethyl (aspartic acid), 2-carboxyethyl (glutamic acid), 3-guanidinopropyl (arginine), 4-aminobutyl (lysine), sec-butyl (isoleucine), indol-3-ylmethyl (tryptophan), (aminocarbonyl)methyl (asparagine), (aminocarboxyl)ethyl (glutamine) and imidazol-4-ylmethyl (histidine).

Any functional group present in R above can be protected in a manner which is known per se in peptide chemistry. For example, a hydroxy group can be protected in the form of a readily cleavable ether such as the tert-butyl, benzyl or tetrahydropyranyl ether or in the form of a readily cleavable ester such as the acetate. A mercapto group can be protected, for example, by a tert-butyl, benzyl or like group. An amino group can be protected, for example by a tert-butoxycarbonyl, benzyloxycarbonyl, benzyloxymethyl, formyl, trityl, trifluoroacetyl, 2-(biphenylyl)isopropoxycarbonyl or isobornyloxycarbonyl group or in the form of a phthalimido or like group. A carboxy group can be protected, for example, in the form of a readily cleavable ester such as the methyl, ethyl, tert butyl or like ester.

An amino group present in R above can be acylated with an acyl group derived from an aliphatic carboxylic acid (e.g. a $C_{1-6}$alkanoic acid such as acetic acid, propionic acid, butyric acid etc.), from an aromatic carboxylic acid (e.g. benzoic acid or a benzoic acid which is substituted by one or more substituents selected from $C_{1-6}$alkyl, $C_{1-6}$alkoxy, carboxy, halogen, trifluoromethyl etc.) or from an araliphatic carboxylic acid (e.g. an aryl$C_{1-6}$alkanoic acid such as phenylacetic acid) or with an aminocarboxylic acid. Examples of such aminocarboxylic acids are α-amino acids such as the natural α-amino acids (e.g. glycine, alanine etc.). Alternatively, an amino group present in R above can be sulphonylated with, for example, a $C_1$-$C_6$-alkanesulphonic acid (e.g. methanesulphonic acid) or an arylsulphonic acid (e.g. benzenesulphonic acid or p-toluenesulphonic acid).

A carboxyl group present in R above can be amidated in a conventional manner. Thus, examples of amidated carboxyl groups are the aminocarbonyl, ($C_1$-$C_6$-alkyl)aminocarbonyl, di($C_1$-$C_6$-alkyl-aminocarbonyl or arylaminocarbonyl groups as well as a carboxyl group amidated with an aminocarboxylic acid such as a natural α-amino acid (e.g. glycine, alanine etc.).

The term '5 to 7 membered cyclic amine' refers to a 5, 6 or 7 membered saturated ring linked via a ring nitrogen atom to the rest of the molecule, optionally containing —O—, —S— or —$NR^{10}$— (where $R^{10}$ is hydrogen or $C_{1-4}$alkyl) and optionally substituted by an oxo group. Examples of suitable cyclic amines include 5 or 6 membered cyclic amines selected from pyrrolidinyl, piperidinyl, morpholinyl and pyrrolidin-2-onyl.

The 'Het' ring system of formula (i) may be substituted by a halogen atom or a group selected from hydroxyl, $C_{1-6}$alkyl (e.g. t-butyl), nitro, $C_{1-6}$alkoxy, $R^{11}CONH(CH_2)_m—$, $R^{12}NHCO(CH_2)_m—$,

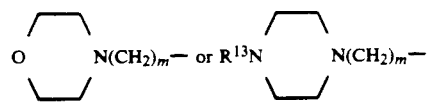

(where m is zero, 1, 2 or 3, $R^{11}$ is $C_{1-6}$alkyl, $R^{12}$ is hydrogen or $C_{1-6}$alkyl and $R^{13}$ is hydrogen or $C_{1-3}$alkyl). The Het ring system of formula (ii) or formula (iii) may be substituted by a halogen atom or a group selected from hydroxyl, $C_{1-3}$ alkyl and $C_{1-3}$ alkoxy.

Examples of suitable 'Het' ring systems include

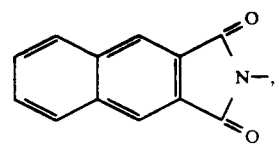

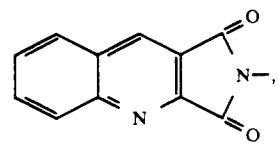

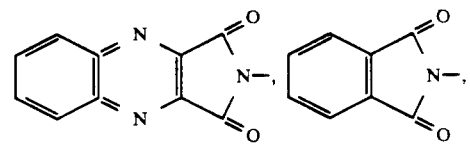

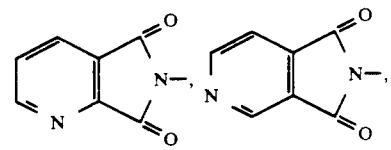

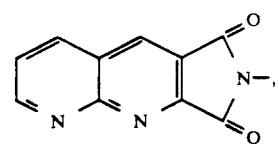

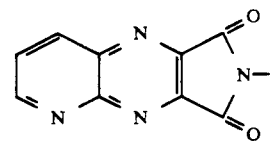

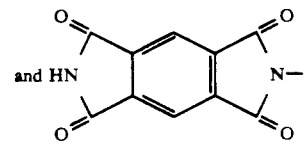

which may each be optionally substituted.

A particular group of compounds of the invention are compounds of formula (I) in which the 'Het' ring system represents

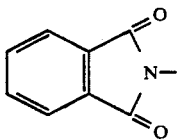

which may be optionally substituted.

Another particular group of compounds of the invention are compounds of formula (I) in which the 'Het' ring system represents

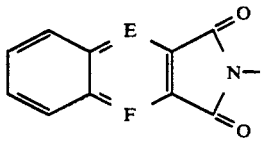

which may be optionally substituted.

$R^1$ preferably represents $C_{3-6}$alkyl such as propyl, iso-butyl or sec-butyl, especially iso-butyl.

Examples of suitable $R^2$ groups include $C_{1-6}$alkyl, arylmethyl and heteroarylmethyl.

Examples of suitable $R^3$ groups include $C_{1-3}$alkyl (e.g. methyl) and $(CH_2)_nX$ where n and X are as defined previously, more particularly n is 1-3 and X is a group $NR^7R^8$ where $NR^7R^8$ forms a 5 or 6 membered cyclic amine as defined above (e.g. morpholinyl).

A preferred group of compounds of the invention are compounds of formula (Ia)

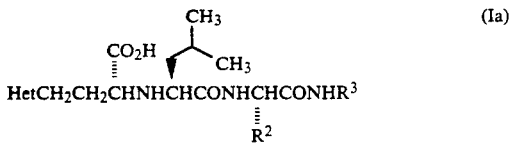

where Het, $R^2$ and $R^3$ are as defined previously, and physiologically acceptable salts and solvates (e.g. hydrates) thereof. Compounds of formula (Ia) in which Het represents an optionally substituted 2,3-dihydro-1,3-dioxo-1H-isoindol-2-yl group may be particularly preferred. Compounds of formula (Ia) in which Het represents a 1,3-dihydro-1,3-dioxo-2H-benz[f]isoindol-2-yl group optionally substituted by a $C_{1-3}$ alkoxy (e.g. methoxy) group may also be particularly preferred.

It is to be understood that the present invention covers all combinations of preferred and particular groups referred to above.

Preferred compounds include:

N-[1-(R)-carboxy-3-(1,3-dihydro-1,3-dioxo-2H-benz[f]isoindol-2-yl)propyl]-L-leucyl-N-methyl-L-phenylalaninamide, N-[1-(R)-carboxy-3-(1,3-dihydro-4-methoxy-1,3-dioxo-2H-benz[f]isoindol-2-yl)propyl]-L-leucyl-N-methyl-L-phenylalaninamide, N-[1-(R)-carboxy-3-(1,3-dihydro-5-methoxy-1,3-dioxo-2H-benz[f]isoindol-2-yl)propyl]-L-leucyl-N-methyl-L-phenylalaninamide, N-[1-(R)-carboxy-3-(1,3-dihydro-1,3-dioxo-2H-benz[f]isoindol-2-yl)propyl]-L-leucyl-N-(morpholinoethyl)-L-leucinamide, N-[1-(R)-carboxy-3-(1,3-dihydro-1,3-dioxo-2H-benz[f]isoindol-2-yl)propyl]-L-leucyl-N-methyl-L-tyrosinamide, N-[1-(R)-carboxy-3-(1,3-dihydro-1,3-dioxo-2H-benz[f]isoindol-2-yl)propyl]-L-leucyl-N-methyl-L-phenylglycinamide, N-[1-(R)-carboxy-3-(1,3-dihydro-1,3-dioxo-2H-benz[f]isoindol-2-yl)propyl]-L-leucyl-N-(morpholinoethyl)-L-phenylalaninamide, and physiologically acceptable salts and solvates (e.g. hydrates) thereof.

As stated hereinabove, the compounds of the present invention act as inhibitors of metalloproteases involved in tissue degradation, which include the mammalian collagenase family of protease enzymes exemplified by interstitial (type 1) collagenase, the stromelysins (also known as proteoglycanases or transins), fibroblast and polymorphonuclear leucocyte gelatinases (also known as collagen-IV-ases) and 'pump-1' (putative metalloprotease 1, uterine metalloprotease). Metalloproteases have been implicated as the enzymes responsible for the destruction of the connective tissues in several chronic inflammatory conditions. There is evidence implicating metalloproteases in the breakdown of articular cartilage and bone in rheumatoid arthritis (Arthritis and Rheumatism, 20, 1231-1239, 1977). Procollagenase has been identified in the synovial fluid of patients with rheumatoid arthritis and immunolocalisation studies have shown that the active enzyme is present at the sites of erosion. D. F. Carmichael et al. have recently demonstrated that large doses of the natural inhibitor of collagenase, TIMP, decreases the severity of arthritis in a collagen-induced model in the mouse (Agents and Actions, 27, 378, 1989). Metalloproteases have also been implicated in the initiation of tumour metastasis/angiogenesis (Nature, 284, 67-68, 1980) and in the pathogenesis of demyelinating diseases of the nervous system (J. Neurochem, 50, 688-694, 1988). The compounds of the present invention are therefore useful in treating or preventing conditions which involve tissue breakdown including rheumatoid arthritis and related diseases in which collagenolytic activity is important. Conditions involving tissue breakdown which may be treated by the use of compounds of the present invention include arthropathy, dermatological conditions, bone resorption, inflammatory diseases, tumour invasion and multiple sclerosis and related disorders involving myelin degradation. The compounds of the present invention can also be used in the promotion of wound healing. Specifically, compounds of the present invention can be used in the treatment of osteopenias such as osteoporosis, hyperparathyroidism, cholesteatoma, rheumatoid arthritis, osteoarthritis, periodontitis, gingivitis, dystrophic epidermolysis bullosa, corneal ulceration, tumour metastasis, tumour growth, angiogenesis, multiple sclerosis, optic neutritis, neuromyelitis optica (Devic's disease), diffuse and transitional sclerosis (Schilder's disease), acute disseminated encephalomyelitis and demyelinating peripheral neuropathies including acute inflammatory demyelinating polyradiculoneuropathies [Landry-Guillain-Barre-Strohl syndrome for motor defects and analogous syndromes for sensory and autonomic (pandysautonomia) deficits], and the chronic and recurrent inflammatory demyelinating polyradiculoneuropathies.

It will be appreciated by those skilled in the art that reference herein to treatment extends to prophylaxis as well as the treatment of established conditions.

As mentioned above, compounds of formula (I) are useful in human or veterinary medicine as they are active inhibitors of metalloproteases involved in tissue degradation.

There is thus provided as a further aspect of the invention a compound of formula (I) or a physiologically acceptable salt or solvate thereof for use in human or veterinary medicine, particularly in the treatment of diseases involving tissue degradation (in particular rheumatoid arthritis and/or tumour metastasis).

According to another aspect of the invention, there is provided the use of a compound of formula (I) or a physiologically acceptable salt or solvate thereof for the manufacture of a medicament for the treatment of diseases involving tissue degradation (in particular rheumatoid arthritis and/or tumour metastasis).

In a further or alternative aspect there is provided a method for the treatment of diseases involving tissue degradation (in particular rheumatoid arthritis and/or tumour metastasis), which method comprises administering to a human or animal subject an effective amount of a compound of formula (I) or a physiologically acceptable salt or solvate thereof.

The capacity of compounds of formula (I) to act as inhibitors of collagenase was determined by using $^3$H collagen fibril substrate (Anal. Biochem., 99, 340–345, 1979) or by using a chromogenic collagenase substrate (Biochemistry, 24, 6730–6734, 1985). For the fibril assay, collagen was $^3$H labelled (Methods in Enzymology, 80, 711, 1981). A 100 μM solution of the inhibitor or dilution thereof was incubated with collagen and collagenase (25 mM TRIS, 150 mM NaCl, 5 mM CaCl$_2$, 0.05% Brij 35, pH 7.5) for 4–16 hours at 37° C. Undigested collagen was pelleted by centrifugation and an aliquot of the radioactive supernatant was counted on a scintillation counter to measure hydrolysis. For the chromogenic assay, a 100 μM solution of inhibitor or dilutions thereof was incubated with chromogenic substrate and collagenase (25 mM TRIS, 150 mM NaCl, 5 mM CaCl$_2$, 1 mM DTNB, 0.05% Brij 35, pH 7.5). Substrate hydrolysis was followed for the 5–10% conversion. The capacity of compounds of formula (I) to act as inhibitors of gelatinase or stromelysin was determined by using $^3$H gelatin substrate. For this assay, tritiated collagen (see above) was gelatinized by heating. A 100 μM solution of the inhibitor or dilutions thereof was incubated with gelatin and enzyme for 2 hour at 37° C. Undigested gelatin was precipitated by the addition of trichloroacetic acid (TCA) and pelleted by centrifugation. An aliquot of the radioactive supernatant was counted on a scintillation counter to measure hydrolysis. The activity in the presence of inhibitor was compared to the control reactions either devoid of inhibitor or devoid or enzyme and the inhibitor concentration effecting 50% inhibition was estimated from the titration curves.

The capacity of compounds of formula (I) to prevent experimental metastases was assessed in mice using the B16/F10 melanoma model according to the method described by T. Kanemoto et al., Proc. Natl. Acad. Sci., USA, 87, 2279-2283 (1990).

Compounds of formula (I) are also tested in the rat adjuvant arthritis model according to the method described by J. N. Taurog et al., J. Exp. Med., 162, 962–978 (1985).

While it is possible that, for use in therapy, a compound of the invention may be administered as the raw chemical it is preferable to present the active ingredient as a pharmaceutical formulation. The invention thus further provides a pharmaceutical formulation comprising a compound of formula (I) or a physiologically acceptable salt or solvate thereof together with one or more pharmaceutically acceptable carriers or excipients. The carrier(s) or excipient(s) must be 'acceptable' in the sense of being compatable with the other ingredients of the formulation and not deleterious to the recipient thereof.

According to another aspect of the invention, there is provided a process for the preparation of a pharmaceutical formulation comprising admixing a compound of formula (I) or a physiologically acceptable salt or solvate thereof with one or more pharmaceutically acceptable carriers or excipients.

Compounds of formula (I) and physiologically acceptable salts and solvates thereof may be formulated for administration by any route, and the appropriate route will depend on the disease being treated. Suitable pharmaceutical formulations include those for oral, rectal, nasal, topical (including buccal and sub-lingual), vaginal or parenteral (including intramuscular, subcutaneous, intravenous and directly into the affected joint) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lypholisation from solution, for constitution with a suitable vehicle, e.g. sterile, pyrogen-free water, before use.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

For topical administration to the eye, the compounds according to the invention may be made up in a solution or suspension in a suitable sterile aqueous or non-aqueous vehicle. Additives such as buffers (e.g. sodium metabisulphite or disodium edeate) and thickening agents such as hypromellose may also be included.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops.

Drops may be formulated with an aqueous or non-aqueous base also comprising one more more dispersing agents, solubilising agents or suspending agents. Liquid sprays are conveniently delivered from pressurised packs.

For administration by inhalation the compounds according to the invention are conveniently delivered from an insufflator, nebuliser or a pressurised pack or other convenient means of delivering an aerosol spray. Pressurised packs may comprise a suitable propellant such as dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The pharmaceutical compositions according to the invention may also contain other active ingredients such as antimicrobial agents, or preservatives.

The compounds of the invention may also be used in combination with other therapeutic agents for example antiinfective agents such as bactericidal or fungicidal agents, antiinflammatory agents or anticancer agents.

The invention thus provides, in a further aspect, a combination comprising a compound of formula (I) or a physiologically acceptable derivative thereof together with another therapeutically active agent, in particular a bactericidal or fungicidal agent, an antiinflammatory agent or an anticancer agent.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention.

Suitable therapeutic agents for use in such combinations include tetracyclin and appropriate non-steroid and steroid antiinflammatory drugs and anticancer agents.

The individual components of such combinations may be administered either sequentially or simultaneously in separate or combined pharmaceutical formulations. Appropriate doses of known therapeutic agents will be readily appreciated by those skilled in the art.

The amount of a compound of the invention required for use in treatment will of course vary not only with the particular compound selected but also with the route of administration, the nature of the condition being treated and the age and condition of the patient and will be ultimately at the discretion of the attendant physician or veterinarian. In general however a suitable dose will be in the range of from about 0.1 to 300 mg/kg of bodyweight per day, particularly from about 1 to 100 mg/kg of bodyweight per day.

An appropriate dosage unit involved in oral administration may generally contain from about 1 to 250 mg, preferably from about 25 to 250 mg, of a compound of formula (I).

The dosage employed for the topical administration will, of course, depend on the size of the area being treated. For the eyes each dose will be typically in the range of from 10 to 100 mg of the compound of formula (I).

For use in the treatment of rheumatoid arthritis the compounds of the invention can be administered by any of the aforementioned routes, particularly by the oral route or by injection. The daily dosage for a 70 kg mammal will be in the range of about 10 mg to 5 g of a compound of formula (I).

Compounds of formula (I) may be prepared by any suitable method known in the art and/or by the following processes which themselves form part of the present invention. In the methods below Het, $R^1$, $R^2$ and $R^3$ are as defined above except where otherwise indicated.

Thus, according to another aspect of the invention, there are provided hereinafter processes for the preparation of a compound of formula (I). A first process (A) for preparing a compound of formula (I) comprises reacting a compound of formula (II)

(where L represents a hydroxyl group or a conventional leaving group and $R^p$ represents a protecting group) with a cyclic imide HetH, followed by the removal of the protecting group(s) present.

The displacement reaction may be carried out in a suitable solvent such as an ether (e.g. tetrahydrofuran), a nitrile (e.g. acetonitrile) or an amide (e.g. dimethylformamide), at a temperature of, for example, 20° to 150° C.

L may represent, for example, a hydroxyl group or a leaving group such as halogen or a group $OSO_2R^{14}$ where $R^{14}$ is an alkyl (e.g. methyl), haloalkyl (e.g. trifluoromethyl) or aryl (e.g. tolyl) group.

When L is a conventional leaving group the reaction is effected in the presence of a base such as an organic base (e.g. triethylamine) or an inorganic base (e.g. sodium hydride).

When L is a hydroxyl group the compound of formula (II) is treated with the cyclic imide HetH in the presence of an activating system such as triphenylphosphine and diethylazodicarboxylate.

Cyclic imides HetH may be prepared using conventional methods, for example by reacting a suitable aromatic bis-carboxylic acid or a corresponding cyclic anhydride with urea.

Another process (B) for preparing a compound of formula (I) comprises coupling a compound of formula (III)

(where $R^P$ is as defined above and $R^q$ represents OH, $-NHCHR^2CO_2H$ or $-NHCHR^2CONHCHR^4CO_2H$) with an appropriate compound of formula (IV)

$$H_2NR^x \qquad (IV)$$

(where $R^x$ represents $R^6$ or $R^3$ as defined above or a group $-CHR^2CONHR^3$), followed by the removal of the protecting group(s) present. The condensation reaction may be carried out in a manner which is known per se in peptide chemistry. Thus, for example, the condensation may be carried out according to an activated ester method, particularly using 1-hydroxybenzotriazole in the presence of a condensation agent such as N,N'-dicyclohexylcarbodiimide and in a suitable solvent (e.g. dimethylformamide).

Another process (C) for preparing a compound of formula (I) comprises introducing a cyclic imido group into a compound of formula (V)

(where $R^P$ is as defined above), followed by the removal of the protecting group(s) present.

The introduction of a cyclic imido group may be carried out in a manner known per se in peptide chemistry. For example, a cyclic imido group may be introduced by reacting a compound of formula (V) with a suitable activated aromatic bis-carboxylic acid derivative in accordance with known methods. Examples of suitable activated aromatic bis-carboxylic acid derivatives include acid anhydrides, mixed anhydrides, chlorides, esters, thioesters etc. Alternatively, activation of the aromatic bis-carboxylic acid may be effected in situ using methods known in peptide chemistry.

Another process (D) for preparing a compound of formula (I) comprises reacting a compound of formula (VI)

with a compound of formula (VII)

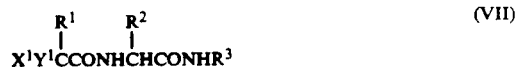

(where $R^P$ is as defined above and X and Y together form an oxo group or X is hydrogen and Y is a group L as defined above when $X^1$ is hydrogen and $Y^1$ is $NH_2$ or alternatively X is hydrogen and Y is $NH_2$ when $X^1$ and $Y^1$ together form an oxo group or $X^1$ is hydrogen and $Y^1$ is a group L as defined above) under conventional conditions of amination or reductive amination as appropriate, followed by the removal of the protecting group(s) present.

In the reductive amination (i.e. where X and Y represent =O and $X^1$ is hydrogen and $Y^1$ is $NH_2$ or X is hydrogen and Y is $NH_2$ and $X^1$ and $Y^1$ represent =O) the condensation reaction may conveniently be carried out in a suitable solvent such as an alcohol (e.g. methanol) or an ether (e.g. tetrahydrofuran) or an aqueous ether (e.g. aqueous tetrahydrofuran) in the presence of a suitable reducing agent such as a borohydride (e.g. sodium borohydride, sodium cyanoborohydride or sodium triacetoxy borohydride) or a dissolving metal (e.g. sodium). Alternatively the in situ formed Schiff's Base may be reduced by catalytic hydrogenation, e.g. in the presence of Raney Nickel or palladium-on-carbon.

The amination process (i.e. where X is hydrogen and Y is a group L and $X^1$ is hydrogen and $Y^1$ is $NH_2$ or X is hydrogen and Y is $NH_2$ and $X^1$ is hydrogen and $Y^1$ is a group L) may be carried out under the conditions described in process (A) above.

Compounds of formula (II) may be prepared from compounds of formula (VIII)

(where $R^P$ is as defined above and $R^a$ is a hydroxyl protecting group). When L in formula (II) is a hydroxyl group the reaction involves removal of the protecting group $R^a$. When L in formula (II) is a leaving group such as halogen or $OSO_2R^{14}$ such groups may be introduced by removing the protecting group $R^a$ followed by conventional displacement reactions.

Compounds of formula (VIII) may be prepared by coupling a compound of formula (IX)

(where $R^a$, $R^P$ and $R^q$ are as defined above) with an appropriate compound of formula (IV) under the general conditions described in process (B) above.

Compounds of formula (III) in which $R^q$ represents $-NHCHR^2CO_2H$ or $-NHCHR^2CONHCHR^4CO_2H$ and compounds of formula (IX) in which $R^q$ represents $-NHCHR^2CO_2H$ or $-NHCHR^2CONHCHR^4CO_2H$ may each be prepared from the corresponding compounds of formula (III) in which $R^q$ represents OH or compounds of formula (IX) in which $R^q$ represents OH by coupling with an appropriate α-aminoacid or sequence of α-aminoacids in a manner which is known per se in peptide chemistry and described in process (B) above.

Compounds of formula (III) in which $R^q$ represents OH may be prepared by reacting a compound of formula (X)

(X)

(where L and $R^p$ are as defined above and $R^b$ is a protecting group) with a cyclic imide HetH under the general conditions described in process (A) above, followed by the removal of the protecting group $R^b$.

Compounds of formula (X) may be prepared from compounds of formula (XI)

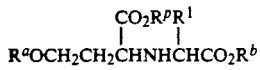
(XI)

(where $R^a$, $R^p$ and $R^b$ are as defined above) under the general conditions described above for preparing compounds of formula (II) from compounds of formula (VIII).

Compounds of formula (IX) in which $R^q$ represents OH may be prepared by removal of the protecting group $R^b$ from compounds of formula (XI).

Compounds of formula (IV) in which $R^x$ is hydrogen, $C_{1-6}$alkyl or $(CH_2)_nX$ are either known amines or may be prepared using methods analogous to those used to prepare the known amines of formula (IV). Compounds of formula (IV) in which $R^x$ is $CHR^4COR^5$ or $CHR^2CONHR^3$ may be prepared according to the methods described in USP 4511504 (Searle).

Compounds of formula (V) and (VII) are either known compounds described in USP 4511504 (Searle) or may be prepared using methods analogous to those used therein to prepare the known compounds of formulae (V) and (VII).

Compounds of formula (VI) may be prepared from compounds of formula (XII)

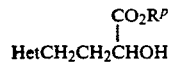
(XII)

(where $R^p$ is as defined above). Thus, compounds of formula (VI) in which X and Y together form an oxo group may be prepared by treating (XII) with a suitable oxidising agent such as pyridinium dichromate, pyridinium dichlorochromate, oxalyl chloride/dimethylsulphoxide, sulphur trioxide-pyridine complex, tetrapropylammonium perruthenate etc. Compounds of formula (VI) in which X is hydrogen and L is a leaving group may be prepared by performing conventional displacement reactions on compounds of formula (XII).

Compounds of formula (VI) in which X is hydrogen and Y is $NH_2$ may be prepared from amino- and carboxyl-protected homoserine by treating said compounds or derivatives thereof in which the hydroxyl group is activated or replaced by a conventional leaving group (as illustrated for compounds of formula (II) above) with a compound HetH according to the general method described in process (A) above, followed by the removal of the protecting groups present.

Compounds of formula (XII) may be prepared by treating compounds of formula (XIII)

(XIII)

(where $R^a$ and $R^p$ are as defined above) with a compound HetH in the presence of an activating system such as triphenylphosphine and diethylazodicarboxylate, followed by the removal of the protecting group $R^a$.

Compounds of formula (XIII) may be prepared by reducing compounds of formula (XIV)

(XIV)

(where $R^a$ and $R^p$ are as defined above) using a suitable reducing agent such as a boron reducing agent (e.g. $BH_3$).

Compounds of formula (XIV) may be prepared from malic acid using conventional protecting means.

Compounds of formula (XI) may conveniently be prepared by reacting a compound of formula (XV)

(XV)

(where $R^a$ and $R^p$ are as defined above) with a compound of formula (XVI)

(XVI)

(where L and $R^b$ are as defined above) under the general conditions described in process (A) above. Alternatively when L is a hydroxyl group the reaction may be effected with activation using triflic anhydride.

Compounds of formula (XV) may be prepared by reducing a suitably protected derivative of aspartic acid, followed by the removal of the amine protecting group (e.g. a benzyloxycarbonyl group). The reduction may conveniently be effected by first treating the derivative of aspartic acid with a chloroformate (e.g. ethyl chloroformate) followed by reduction with a suitable reducing agent such as a borohydride reducing agent (e.g. sodium borohydride).

Compounds of formula (XVI) may be prepared from an α-aminoacid or a derivative thereof in which the carboxyl group is protected by conventional displacement reactions followed, where necessary, by introduction of the protecting group $R^b$.

Another process (E) for preparing a compound of formula (I) comprises deprotecting a protected derivative of a compound of formula (I). It will be appreciated that in the above processes (A)-(D) the removal of the protecting group $R^p$ is required as a step subsequent to the main process step. Thus processes (A)-(D) produce intermediate compounds of formula (XVII)

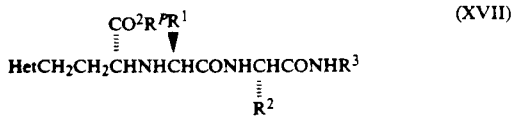

(where $R^p$ is a protecting group as defined hereinafter) which are then deprotected to provide the desired compounds of formula (I).

It will also be appreciated that other functional groups present in appropriate starting materials may need to be protected, and deprotection may thus be required as an intermediate or final step to yield the desired compound. Protection and deprotection of functional groups may be effected using conventional means. Thus, for example, amino groups may be protected by a group selected from aralkyl (e.g. benzyl), acyl or sulphonyl (e.g. allylsulphonyl or tosyl); subsequent removal of the protecting group being effected when desired by hydrolysis or hydrogenolysis as appropriate using standard conditions. Hydroxyl groups may be protected using any conventional hydroxyl protecting group, for example, as described in 'Protective Groups in Organic Chemistry', Ed. J. F. W. McOmie (Plenum Press, 1973) or 'Protective Groups in Organic Synthesis' by Theodora W. Greene (John Wiley and Sons, 1981). Examples of suitable hydroxyl protecting groups include groups selected from alkyl (e.g. methyl, t-butyl or methoxymethyl), aralkyl (e.g. benzyl, diphenylmethyl or triphenylmethyl), heterocyclic groups such as tetrahydropyranyl, acyl (e.g. acetyl or benzoyl) and silyl groups such as trialkylsilyl (e.g. t-butyldimethylsilyl). The hydroxyl protecting groups may be removed by conventional techniques. Thus, for example, alkyl, silyl, acyl and heterocyclic groups may be removed by solvolysis, e.g. by hydrolysis under acidic or basic conditions. Aralkyl groups such as triphenylmethyl may similarly be removed by solvolysis, e.g. by hydrolysis under acidic conditions. Aralkyl groups such as benzyl may be cleaved by hydrogenolysis in the presence of a Noble metal catalyst such as palladium-on-charcoal. Silyl groups may also conveniently be removed using a source of fluoride ions such as tetra-n-butylammonium fluoride. Carboxyl protecting groups, including $R^p$ above, may conveniently be represented by appropriate hydroxyl protecting groups above with deprotection effected according to the methods described above. Thus, for example the group $R^p$ may conveniently represent an alkyl (e.g. methyl or t-butyl) group which can be removed by acid hydrolysis (e.g. using trifluoroacetic or hydrochloric acid) or an aralkyl (e.g. benzyl) group which can be removed by catalytic hydrogenolysis.

Compounds of formulae (II), (III), (VI), (XI), (XII) and (XVII) are novel intermediates and as such form further aspects of the present invention. Preferred intermediates of formula (XVII) are those compounds in which $R^p$ represents t-butyl.

Particular isomers of formula (I) may either be prepared from starting materials having the desired stereochemistry or by epimerisation or resolution at an appropriate stage in the synthesis of the required compounds of formula (I). Epimerisation and resolution may be effected by conventional means.

It will be appreciated that in addition to the process steps outlined above it may be convenient to utilise the general process concepts described in processes (A)-(E) above to effect suitable conversions on appropriate intermediates prior to the final step reaction.

When it is desired to prepare an acid addition salt of a compound of formula (I) the product of any of the above procedures may be converted into a salt by treatment of the resulting free base with a suitable acid using conventional methods.

Physiologically acceptable acid addition salts of the compounds of formula (I) may be prepared by reacting a compound of formula (I) in the form of the free base with an appropriate acid optionally in the presence of a suitable solvent such as an ester (e.g. ethyl acetate) or an alcohol (e.g. methanol, ethanol or isopropanol).

Inorganic basic salts may be prepared by reacting the free base of a compound of formula (I) with a suitable base e.g. an alkoxide such as sodium methoxide optionally in the presence of a solvent (e.g. an alcohol such as methanol).

Physiologically acceptable salts may also be prepared from other salts, including other physiologically acceptable salts, of the compounds of formula (I) using conventional methods.

Solvates (e.g. hydrates) of a compound of formula (I) may be formed during the work-up procedure of one of the aforementioned process steps.

The following Preparations and Examples illustrate the invention but do not limit the invention in any way. All temperatures are in °C.

INTERMEDIATE 1

4-Methyl-D-aspartate hydrochloride

Methanol (210 mL) was slowly stirred and cooled to −10° and thionyl chloride (31 mL) was added dropwise over 45 min. D-Aspartic acid (40 g) was added over 5 min and the reaction stirred for 3 h while warming to 21°. Diethyl ether (600 mL) was added slowly and the mixture cooled to −10°. The resulting solid was filtered, washed with diethyl ether (200 mL) and dried in vacuo to afford the title compound as a white solid (33.4 g.)

$[\alpha]_D$ −15.7° (c=0.7;MeOH).

Analysis Found: C, 32.88; H, 5.40; N, 7.63; $C_5H_9NO_4HCl$ requires: C, 32.71; H, 5.49; N, 7.63%.

INTERMEDIATE 2

N-[(Phenylmethoxy)carbonyl]-D-aspartic acid, 1-(1,1-dimethylethyl)-4-methyl ester Intermediate 1 (32 g) was dissolved in a mixture of water (250 mL) and dioxane (250 mL), and sodium carbonate (92.4 g) was added slowly with stirring. Benzylchloroformate (25 mL) was added and the mixture stirred for 15 h at 23°. Ethyl acetate (250 mL) was added and the mixture was acidified to pH2 with concentrated HCl. The organic phase was separated and the aqueous phase extracted with ethyl acetate (2×150 mL). The combined organic layers were washed with brine, dried (MgSO$_4$) and evaporated. The residue was dissolved in methylene chloride (800 mL) and treated with concentrated H$_2$SO$_4$. Isobutylene (200 mL) was condensed into the stirred mixture and the solution was left to stand for 15 h. The mixture was neutralized with sodium bicarbonate and the organic phase was washed with water and brine, dried (Na$_2$SO$_4$) and evaporated. The resulting oil was purified by silica chromatography using cyclohexane:ethyl acetate (4:1) as eluent to afford the title compound as a clear oil (31.8 g).

$[\alpha]_D$ +14.04°(c=1.14; MeOH).

Analysis Found: C, 60.13; H, 7.06; N, 4.19; $C_{17}H_{23}NO_6$ requires: C, 60.52; H, 6.87; N, 4.15%.

INTERMEDIATE 3

N-[(Phenylmethoxy)carbonyl]-D-aspartic acid, 1,1-dimethylethyl ester

A solution of Intermediate 2 (31.3 g) in methanol (120 mL) was treated with 1N NaOH (102 mL) and the resulting yellow solution stirred at 21° for 2 h. The reaction mixture was concentrated in vacuo to about 30 mL and partitioned between water (250 mL) and ether (250 mL). The aqueous layer was washed with ether (250 mL) and layered with more ether (250 mL). The mixture was stirred vigorously and acidified to pH2 with concentrated HCl. The organic layer was separated and the aqueous layer extracted with ether (250 mL). The combined extracts were washed with brine, dried ($Na_2SO_4$) and evaporated to afford the title compound as a yellow oil (29.4 g).

$[\alpha]_D + 11.6°$ (c=0.86; MeOH).

Analysis Found: C, 58.30; H, 6.63; N, 4.36; $H_2O$, 1.0; $C_{16}H_{21}NO_6.0.2H_2O$ requires: C, 58.78; H, 6.60; N, 4.28; $H_2O$, 1.1%.

INTERMEDIATE 4

N-[(Phenylmethoxy)carbonyl]-D-homoserine, 1,1-dimethylethyl ester

A solution of Intermediate 3 (29.23 g) in dry tetrahydrofuran (120 mL) at −10° was treated with N-methylmorpholine (10 mL). The mixture was stirred for 3 min. and ethyl chloroformate (8.7 mL) was added dropwise. The mixture was warmed to 23° over 15 min. and filtered. The filtrate was added dropwise over 30 min. to a vigorously stirred mixture of sodium borohydride (7.7 g) in water (60 mL) at 3°. The cooling bath was removed, the mixture stirred at 21° for 3h, then cooled to 0° and acidified to pH2 with concentrated HCl. The mixture was extracted with ethyl acetate (3×200 mL) and the combined organic extracts were washed with brine, dried ($Na_2SO_4$) and evaporated to furnish a clear oil. Purification by silica chromatography using methylene chloride-acetone (9:1) as eluent afforded the title compound as a clear oil (21.6 g).

$[\alpha]_D + 30.4°$ (c=1.81; MeOH).

Analysis Found: C, 62.12; H, 7.49; N, 4.53; $C_{16}H_{23}NO_5$ requires: C, 61.75; H, 7.71; N, 4.52%

INTERMEDIATE 5

N-[(Phenylmethoxy)carbonyl]-O-[(1,1-dimethylethyl)-dimethylsilyl]-D-homoserine, 1,1-dimethylethyl ester A solution of Intermediate 4 (26 g) in dry dimethylformamide (300 mL) was treated with imidazole (5.72 g) and then t-butyldimethylsilyl chloride (12.7 g) and the mixture stirred at 21° for 18 h. The mixture was poured into a mixture of 1:1 ethyl acetate-2N HCl (1000 mL) and the organic phase was separated and washed with 2N HCl (2×300 mL). The combined aqueous phases were extracted with ethyl acetate (2×250 mL) and the combined organic layers were washed with brine, dried ($Na_2SO_4$) and evaporated to give a clear oil. Purification by silica chromatography using 4:1 cyclohexane-ethyl acetate as eluent furnished the title compound as a clear oil (20.93 g).

$[\alpha]_D + 28.26°$ (c=0.92; MeOH).

Analysis Found: C, 62.25; H, 9.08; N, 3.30; $C_{22}H_{37}NO_5Si$ requires: C, 62.37; H, 8.80; N, 3.31%.

INTERMEDIATE 6

O-[(1,1-Dimethylethyl)dimethylsilyl]-D-homoserine, 1,1-dimethylethyl ester

A solution of Intermediate 5 (26.2 g) in ethanol (200 mL) was shaken with 10% palladium on carbon (2.7 g) in a hydrogen atmosphere (50 psi) at 21° for 3 h. The catalyst was removed by filtration through celite, and the solvent was evaporated to afford the title compound as a clear oil (17.3 g).

$[\alpha]_D - 10.74°$ (c=1.21; MeOH).

INTERMEDIATE 7

2-(R)-Hydroxy-4-methylpentanoic acid, phenylmethyl ester

A solution of D-leucine (26.2 g) in 1N sulphuric acid (300 mL) was cooled to 0° and treated dropwise with a solution of $NaNO_2$ (25.5 g) in water (50 mL) over 0.5 h. The mixture was stirred for 3 h at 0°, allowed to warm up to 23° for 2 h and extracted with ether (3×100 mL). The combined organic layers were washed with brine (100 mL), dried ($MgSO_4$) and evaporated to afford a white solid (21.0 g). This was dissolved in methanol (200 mL) and treated with a solution of sodium hydroxide (6.5 g) in water (35 mL). After 5 min. the organic solvent was evaporated and the resulting aqueous solution was lyophilized overnight. The resulting solid was slurried in dimethylformamide (400 mL) and treated with benzyl bromide (20 mL). The mixture was stirred at 23° for 18 h and the solvent removed by evaporation. The residue was treated with 2N HCl (200 mL) and extracted with ethyl acetate (3×150 mL). The combined organic layers were washed with aqueous sodium bicarbonate, water, dried ($MgSO_4$) and evaporated to afford the title compound as a light golden oil (32.6 g).

$[\alpha]_D + 15.2°$ (c=1.3; $CHCl_3$).

Analysis Found: C, 69.88; H, 8.43; $C_{13}H_{18}O_3$ requires: C, 70.24; H, 8.16%.

INTERMEDIATE 8

N-[(R)-1-[(1,1-Dimethylethoxy)carbonyl]-3-[[(1,1-dimethylethyl)dimethylsilyl]oxy]propyl]-L-leucine, phenylmethyl ester A solution of Intermediate 7 (7.4 g) in dry methylene chloride (100 mL) was added to a cooled (0°) solution of trifluoromethanesulfonic anhydride (9.40 g) in dry methylene chloride (100 mL). 1,8-Bis(dimethylamino)-naphthalene (7.14 g) was added and the resulting orange mixture stirred at 0° for 30 min. A solution of Intermediate 6 (9.65 g) in dry dioxane (90 mL) was added dropwise along with 1,8-bis(dimethylamino)naphthalene (7.14 g) and the mixture stirred at 21° for 15 h. The mixture was filtered and the filtrate was diluted with ethyl acetate (300 mL), washed with water (2×200 mL), brine (250 mL), dried ($Na_2SO_4$) and evaporated to give a brown oil. Purification by silica chromatography using 9:1 cyclohexane-ether as eluent afforded the title compound as a yellow oil (11.92 g).

$[\alpha]_D - 8.1°$ (c=0.99; $CHCl_3$).

Analysis Found: C, 65.47; H, 9.78; N, 2.78; $C_{27}H_{47}NO_5Si$ requires: C, 65.70; H, 9.60; N, 2.80%.

INTERMEDIATE 9

N-[(R)-1-((1,1-Dimethylethoxy)carbonyl)-3-[[(1,1-dimethylethyl)dimethylsilyl]oxy]propyl]-L-leucine A solution of Intermediate 8 (1.11 g) in ethanol (25 mL) was treated with 10% palladium on carbon (120 mg) and the mixture shaken in a hydrogen atmosphere (40 psi) for 2 hr. The catalyst was removed by filtration through celite and evaporation of the solvent afforded the title compound as a yellow oil (950 mg).

INTERMEDIATE 10

N-[1-(R)-((1,1-Dimethylethoxy)carbonyl)-3-[((1,1-dimethylethyl)dimethylsilyl)oxy]-propyl]-L-leucyl-N-methyl-L-phenylalaninamide A solution of Intermediate 9 (478 mg) in dry dimethylformamide (5 mL) was cooled to 5° and treated with 1-hydroxybenzotriazole hydrate (184 mg) and dicyclohexylcarbodiimide (248 mg). The mixture was stirred for 3 min. and N-methyl-L-phenylalaninamide (214 mg) was added. The cooling bath was removed and the mixture stirred at 21° for 15 h. The mixture was filtered through celite and the solvent evaporated to afford a yellow oil. Purification by silica chromatography using 4:1 methylene chloride-acetone as eluent afforded the title compound as a cream foam (289 mg).

Analysis Found: C, 63.83: H, 9.22; H 7.40. $C_{30}H_{53}N_3O_5Si$ requires: C, 63.90; H, 9.48; N, 7.45%.

INTERMEDIATE 11

N-[1-(R)-((1,1-Dimethylethoxy)carbonyl)-3-hydroxypropyl]-L-leucyl-N-methyl-L-phenylalaninamide Intermediate 10 (200 mg) was dissolved in a mixture of acetic acid (9 mL) and water (1 mL) and stirred at 45° for 15 h. The solvents were evaporated and the residue was dissolved in ethyl acetate (20 mL) and washed with aqueous sodium bicarbonate. The organic layer was dried (MgSO$_4$) and evaporated. The residue was purified by silica chromatography using 2:1 methylene chloride-acetone as eluent to give the title compound as a white foam (143 mg).

NMR (CDCl$_3$) δ 7.52 (1H, d, J=8 Hz), 7.20 (5H, m), 6.80 (1H, brm), 4.68 (1H, q, J=7 Hz), 3.73 (2H, m), 3.36 (1H, m), 3.00 (1H, m), 3.0–3.3 (2H, m), 2.75 (3H, d, J=5 Hz), 1.42 (9H, s), 1.0–1.9 (5H, m), 0.86 (6H, m).

INTERMEDIATE 12

α-(S)-[((1,1-Dimethylethoxy)carbonyl)amino]-N-methyl-2-naphthalenepropanamide 1,1-Carbonyldiimidazole (0.58 g) was added to a stirred solution of α-(S)-[[(1,1-dimethylethoxy)carbonyl]amino]-N-methyl-2-naphthalenepropanoic acid (1.02 g) in methylene chloride (20 mL) and stirring was continued at 21° for 20 min before adding methylamine (2 mL, 9M solution in methylene chloride) and then stirring for a further 3 h. The reaction mixture was washed with water (20 mL), 1N HCl (25 mL), aqueous sodium bicarbonate (25 mL) and brine (30 mL) then dried (Na$_2$SO$_4$) and concentrated to give the title compound as a white solid (1.027 g). Mp. 177°–179°.

[α]$_D$+33.62° (c=1.16, MeOH).

INTERMEDIATE 13

α-(S)-Amino-N-methyl-2-naphthalenepropanamide

A solution of Intermediate 12 (0.665 g) in trifluoroacetic acid (10 mL) was allowed to stand at 21° for 20 min before concentrating in vacuo. The residue was dissolved in ethyl acetate (5 mL) and washed with aqueous sodium bicarbonate (20 mL), and brine (20 mL) then dried (Na$_2$SO$_4$) and concentrated in vacuo to give the title compound as a white solid (0.44 g). Mp. 127°–128°.

NMR (CDCl$_3$) δ 7.2–7.9 (8H, m), 3.72 (1H, dd, J=9, 4 Hz), 3.46 (1H, dd, J=13, 3 Hz), 2.86 (1H, m), 2.83 (3H, d, J=5 Hz), 1.42 (2H, br s).

INTERMEDIATE 14

N-[1-(R)-((1,1-Dimethylethoxy)carbonyl)-3-[[(1,1-dimethylethyl)dimethylsilyl]oxy]propyl]-L-leucyl-N-methyl-3-(2-naphthalenyl)-L-alaninamide (0.209 g)

Prepared as described for Intermediate 10 using α-(S)-amino-N-methyl-2-naphthalenepropanamide (0.207 g).

NMR (CDCl$_3$) δ 8.00 (1H, d, J=9 Hz), 7.3–7.9 (8H, m), 4.88 (1H, m), 3.70 (2H, m), 3.48 (1H, dd, 14, 8 Hz), 3.37 (1H, m), 3.21 (1H, dd, J=14, 5 Hz), 2.85 (1H, m), 2.79 (3H, d, J=5 Hz), 1.4–2.0 (5H, m), 1.38 (9H, s), 0.76 (3H, d, J=7 Hz), 0.69 (3H, d, J=7 Hz), 0.02 (6H, s).

Fast Atom bombardment MS; m/e Found: 614 (MH$^+$).

INTERMEDIATE 15

N-[1-(R)-((1,1-Dimethylethoxy)carbonyl)-3-hydroxypropyl]-L-leucyl-N-methyl-3-(2-naphthalenyl)-L-alaninamide (0.10 g)

Prepared by deprotection of Intermediate 14 following conditions similar to those described for the preparation of Intermediate 11.

NMR (CDCl$_3$) δ 7.3–7.9 (8H, m), 6.82 (1H, m), 4.78 (1H, q, J=7 Hz), 3.62 (2H, m), 3.32 (3H, m), 2.96 (1H, m), 2.77 (3H, d, J=5 Hz), 1.0–2.0 (5H, m), 1.39 (9H, s), 0.78 (3H, d, J=6 Hz), 0.72 (3H, d, J=6 Hz).

INTERMEDIATE 16

N-[1-(R)-((1,1-Dimethylethoxy)carbonyl)-3-[[(1,1-dimethylethyl)dimethylsilyl]oxy]propyl]-L-leucyl-N-methyl-L-tryptophanamide (0.5 g)

Prepared as described for Intermediate 10 using N-methyl-L-tryptophanamide (0.372 g).

[α]$_D$−18.7° (c=0.96, MeOH)

Analysis Found: C, 63.87; H, 8.88; N, 9.20. $C_{32}H_{54}N_4O_5Si$ requires: C, 63.75; H, 9.03; N, 9.29%.

INTERMEDIATE 17

N-[1-(R)-((1,1-Dimethylethoxy)carbonyl)-3-hydroxypropyl]-L-leucyl-N-methyl-L-tryptophanamide (0.196 g)

Prepared as described for Intermediate 11 by deprotection of Intermediate 16 (0.38 g).

[α]$_D$−9.4° (c=0.97, MeOH).

NMR (DMSO-d$_6$) δ 10.81 (1H, br s), 8.01 (1H, d, J=8 Hz), 7.81 (1H, m), 7.55 (1H, d, J=8 Hz), 7.30 (1H, d, J=8 Hz), 6.9–7.12 (3H, m), 4.4–4.6 (2H, m), 3.3–3.05 (m, obscured by H$_2$O), 2.85–3.2 (4H, m), ca 2.53 (3H, m, obscured by DMSO), 1.5–1.8 (3H, m), 1.36 (9H, s), 1.1–1.3 (2H, m), 0.82 (3H, d, J=6 Hz), 0.79 (3H, d, J=6 Hz).

INTERMEDIATE 18

4-(Acetylamino)-1,2-benzenedicarboxylic acid, diethyl ester

A solution of diethyl 4-aminophthalate (660 mg) in methylene chloride (40 mL) at 0° was treated with pyridine (0.25 mL) and acetyl chloride (0.22 mL). The reaction mixture was allowed to warm to 23° and stirred for 16 h. The reaction mixture was partitioned between saturated aqueous sodium bicarbonate and methylene chloride. The organic layer was washed with water, 2N hydrochloric acid and brine, dried (MgSO$_4$) and evaporated. The residue was dissolved in ethyl acetate, which upon standing afforded the title compound as white crystals (350 mg). M.p. 118°-121°.

NMR (CDCl$_3$) δ 7.78 (2H, s), 7.68 (1H, s), 4.35 (4H, m), 2.19 (3H, s), 1.36 (6H, m).

INTERMEDIATE 19

4-(Acetylamino)-1,2-benzenedicarboxylic acid

A solution of Intermediate 18 (506 mg) in methanol (2 mL) and water (15 mL) was treated with sodium hydroxide (247 mg) and heated at 60° for 8 h. The solvent was evaporated, the solution acidified with 2N hydrochloric acid (3.1 mL) and extracted with ethyl acetate. The combined organic layers were dried (MgSO$_4$) and evaporated to afford the title compound (324 mg) as a pale yellow semi-solid.

NMR (DMSO-d$_6$) δ 10.29 (1H, s), 7.82 (1H, s), 7.69 (2H, s), 2.07 (3H, s).

INTERMEDIATE 20

N-(2,3-Dihydro-1,3-dioxo-1H-isoindol-5-yl)acetamide

Intermediate 19 (163 mg) and urea (90 mg) were combined and heated at 170° for 2 h. The mixture was cooled and triturated with water (30 mL) and the resulting solid was collected by filtration to yield the title compound (141 mg) as a tan solid. M.p.>250°.

NMR (DMSO-d$_6$) δ 11.19 (1H,s), 8.13 (1H, s,), 7.81 (2H, m), 2.11 (3H, s).

INTERMEDIATE 21

4-Morpholino-1,2-benzenedicarboxylic acid, diethyl ester

A solution of dihydrofuran (202 mg) in methanol (10 mL) at −42° was treated with ozone until a blue color developed. Nitrogen was bubbled through the reaction mixture until the blue color dissipated. The reaction mixture was treated with sodium cyanoborohydride (430 mg) at −42° for 15 min, then a solution of diethyl 4-aminophthalate (650 mg) in methanol (14 mL) was added, and the reaction mixture allowed to warm to 0° for 2 h. The reaction was quenched with acetic acid (1.2 mL), and the solvent evaporated. The residue was taken up in methylene chloride (100 mL) and 1N sodium hydroxide (50 mL), and the aqueous layer was extracted with methylene chloride (2×50 mL). The combined organic layers were washed with brine, dried (Na$_2$SO$_4$), and evaporated to a yellow oil. The yellow oil was purified by chromatography on silica using 70% hexane-ethyl acetate as eluent to afford the title compound (510 mg) as a pale yellow oil.

NMR (CDCl$_3$) δ 7.79 (1H, d, J=8.8 Hz), 6.95 (1H, d, J=2.7 Hz), 6.89 (1H, dd, J=2.4, 8.4 Hz), 4.36 (2H, q, J=7.5 Hz), 4.30 (2H, q, J=6.9 Hz), 3.83 (4H, m), 3.27 (4H, m), 1.35 (6H, m).

INTERMEDIATE 22

4-Morpholino-1,2-benzenedicarboxylic acid

A solution of Intermediate 21 (503 mg) in methanol (1 mL) and water (10 mL) was treated with sodium hydroxide (202 mg) and heated at 60° for 6 h. The solvent was evaporated, the solution acidified with 2N hydrochloric acid (2.52 mL) and extracted with ethyl acetate. The combined organic layers were dried (MgSO$_4$) and evaporated to afford the title compound (384 mg) as a pale yellow solid. M.p. 178°-80°.

NMR (DMSO-d$_6$) δ 7.65 (1H, d, J=8.8 Hz), 6.98 (1H, dd, J=2.4, 8.8 Hz), 6.93 (1H, s), 3.70 (4H, m), 3.23 (4H, m).

INTERMEDIATE 23

2,3-Dihydro-5-morpholino-1H-isoindol-1,3-(2H)-dione (100 mg).

Prepared as described for Intermediate 20 using Intermediate 22 (167 mg). M.p. 238°-40°.

NMR (DMSO-d$_6$) δ 10.94 (1H, s), 7.60 (1H, d, J=8.1 Hz), 7.25 (2H, m), 3.73 (4H, m), 3.35 (4H, m).

INTERMEDIATE 24

N-(Morpholinoethyl)-L-leucinamide, bis[4-methylbenzenesulphonate]

A solution of N-[(1,1-dimethylethoxy)carbonyl]-L-leucine hydrate (10.4 g), 4-(aminoethyl)morpholine (5.5 g) and 1-hydroxybenzotriazole hydrate (3 g) in dry methylene chloride (100 mL) was treated with dicyclohexylcarbodiimide (9.45 g) and the mixture stirred at 23° for 18 h. The mixture was filtered through celite and the filtrate was washed with aqueous sodium bicarbonate solution, dried (Na$_2$SO$_4$) and evaporated to afford an amber gum. This was dissolved in acetonitrile (100 mL) and treated with 4-toluenesulfonic acid hydrate (24.1 g) and the mixture heated under reflux for 3 h. The cooled solution was diluted with ether (300 mL) and the resulting solid collected by filtration to give the title compound (18.6 g) a sample of which was crystallized from acetonitrile-ether. M.p. 168°-9°.

NMR (DMSO-d$_6$) δ 8.50 (m, 1H), 7.90 (m, 2H), 7.22 (d, J=8.3 Hz, 4H), 6.87 (d, J=7.8 Hz, 4H), 3.80-2.80 (m, 15H), 2.03 (s, 6H), 1.30 (m, 3H), 0.61 (m, 6H).

INTERMEDIATE 25

N-[1-(R)-((1,1-Dimethylethoxy)carbonyl)-3-[((1,1-dimethylethyl) dimethylsilyl)oxy]propyl]-L-leucyl-N-(morpholinoethyl)-L-leucinamide A solution of Intermediate 9 (900 mg), 1-hydroxybenzotriazole hydrate (200 mg), Intermediate 24 (1.42 g) and dicyclohexylcarbodiimide (500 mg) in dry methylene chloride (30 mL) was treated with triethylamine (1 mL) and the mixture stirred for 15 h at 23°. The mixture was filtered through celite and the filtrate was washed with aqueous sodium bicarbonate solution. The organic layer was dried (Na$_2$SO$_4$) and evaporated. The residue was purified by silica chromatography using ethyl acetate then 2% methanol-ethyl acetate as eluent to give the title compound as a gum (900 mg).

NMR (CDCl$_3$) δ 7.96 (d, J=9 Hz), 7.21 (m), 4.12 (m), 3.80-3.60 (m), 3.45 (m), 3.34 (m), 3.02 (m), 2.45 (m), 2.00-1.20 (br m), 1.44 (s), 0.89 (m), 0.06 (s).

INTERMEDIATE 26

N-[1-(R)-((1,1-Dimethylethoxy)carbonyl)-3-hydroxypropyl]-L-leucyl-N-(morpholinoethyl)-L-leucinamide A solution of Intermediate 25 (900 mg) in acetic acid (45 mL) and water (5 mL) was heated at 45° for 3 h. The solvents were evaporated and the residue dissolved in ethyl acetate and washed with aqueous sodium bicarbonate solution. The organic layer was dried (MgSO$_4$) and evaporated. Purification of the residue by silica chromatography using ethyl acetate then 5% methanol-ethyl acetate as eluent afforded the title compound as a white foam (500 mg).

INTERMEDIATE 27

N-[(R)-1-((1,1-Dimethylethoxy)carbonyl)-3-hydroxypropyl]-L-leucine, phenylmethyl ester A solution of Intermediate 8 (5 g) in acetic acid (100 mL) and water (15 mL) was heated at 45° for 4 h. The solvents were evaporated and the residue dissolved in ethyl acetate (100 mL) and washed with aqueous bicarbonate solution. The organic layer was dried (MgSO$_4$) and evaporated. The residue was purified by silica chromatography using 10% ethyl acetate-hexane as eluent to furnish the title compound as an amber oil (2.5 g).

NMR (CDCl$_3$) δ 7.35 (m, 5H), 5.12 (AB system, 2H), 3.79 (t, J=5.2 Hz, 2H), 3.35 (m, 2H), 2.00–1.50 (m, 7H), 1.44 (s, 9H), 0.89 (d, J=6.6 Hz, 6H).

INTERMEDIATE 28

N-[(R)-1-((1,1-Dimethylethoxy)carbonyl)-3-(1,3-dihydro-1,3-dioxo-2H-benz[f]isoindol-2-yl)propyl]-L-leucine, phenylmethyl ester A solution of Intermediate 27 (2.5 g), triphenylphosphine (1.85 g) and 1,3-dihydro-1,3-dioxo-2H-benz[f]isoindole (1.4 g) in dry tetrahydrofuran (100 mL) was cooled to 0° and treated with diethylazidodicarboxylate (1.1 mL). The resulting mixture was allowed to warm up to 23° over 24 h and the solvent removed by evaporation. The residue was purified by silica chromatography using methylene chloride as eluent to afford a light yellow solid. Trituration with methanol (20 mL) and filtration gave the title compound as a white solid (1.9 g) which was crystallised from methanol. M.p. 136°–7°.

NMR (CDCl$_3$) δ 8.32 (s, 2H), 8.04 (m, 2H), 7.69 (m, 2H), 7.33 (m, 5H), 5.10 (AB system, J$_{ab}$=12.4 Hz, 2H), 3.87 (m, 2H), 3.38 (t, J=7.0 Hz, 1H), 3.22 (dd, J=5.1 Hz, J=6.3 Hz, 1H), 2.25 (br s, 1H), 2.10–1.70 (m, 5H), 1.47 (s, 9H), 0.90 (d, J=6.6 Hz, 6H).

Analysis Found: C, 70.69; H, 6.87; N, 4.98; C$_{33}$H$_{38}$N$_2$O$_6$ requires: C, 70.95; H, 6.86; N, 5.01%.

INTERMEDIATE 29

N-[(R)-1-((1,1-Dimethylethoxy)carbonyl)-3-(1,3-dihydro-1,3-dioxo-2H-benz[f]isoindol-2-yl)propyl]-L-leucine A solution of Intermediate 28 (1.9 g) in ethyl acetate (50 mL) was shaken with 10% palladium on carbon (500 mg) in a hydrogen atmosphere (50 psi) for 24 h. The catalyst was removed by filtration through celite and the solvent evaporated. The residue was purified by silica chromatography using 50% ethyl acetate-hexane as eluent to afford the title compound as a cream solid (1.5 g) which was crystallised from ethyl acetate-hexane. M.p. 168°–9°.

NMR (CDCl$_3$) δ 8.34 (s, 2H), 8.05 (m, 2H), 7.70 (m, 2H), 3.87 (m, 2H), 3.31 (m, 2H), 2.20–1.60 (m, 5H), 1.46 (s, 9H), 0.95 (d, J=6.6 Hz, 6H).

Analysis Found: C, 66.58; H, 6.90; N, 5.98; C$_{26}$H$_{32}$N$_2$O$_6$ requires: C, 66.65; H, 6.88; N, 5.98%.

INTERMEDIATE 30

1,3-Dihydro-2H-pyrrolo[3,4-b]quinoline-1,3-dione

Quinoline-2,3-dicarboxylic acid (1.29 g) and urea (709 mg) were ground together and heated at 170° for 3 h. The cooled mass was treated with water (50 mL) and triturated. The resulting solid was filtered, washed with water, and air dried to give the title compound as a white solid (450 mg). M.p.>300°.

NMR (DMSO-d$_6$) δ 8.67 (s, 1H), 8.03 (m, 2H), 7.74 (br t, 1H), 7.57 (br t, 1H).

INTERMEDIATE 31

1,8-Naphthyridine-2,3-dicarboxylic acid, diethyl ester

A suspension of 2-aminopyridine-3-carboxaldehyde (8.67 g) in absolute ethanol (500 mL) was treated with piperidine (1.7 mL) and sodium diethyloxalacetate (29.84 g) and heated to reflux for 18 h. The solvent was evaporated and the residue purified by chromatography on silica using 70% ethyl acetate-hexane as eluent to afford the title compound (2.6 g). M.p. 83°–85°.

NMR (CDCl$_3$) δ 9.26 (1H, dd, J=1.8, 2.4 Hz), 8.86 (1H, s), 8.35 (1H, dd, J=1.8, 6 Hz), 7.64 (1H, dd, J=4.2, 3.9 Hz), 4.53 (2H, q, J=6.9 Hz), 4.45 (2H, q, J=7.2 Hz), 1.46 (3H, t, J=7.2 Hz), 1.43 (3H, t, J=7.2 Hz).

INTERMEDIATE 32

1,8-Naphthyridine-2,3-dicarboxylic acid

A solution of Intermediate 31 (2.3 g) in ethanol (5 mL) and water (70 mL) was treated with sodium hydroxide (1.13 g) and heated at 65° for 16 h. The solution was allowed to cool, and acidified with concentrated hydrochloric acid. The precipitate was filtered, washed with water, and dried to give the title compound (1.05 g) as a pale yellow solid. M.p. 199°–202°.

NMR (DMSO-d6) δ 9.23 (1H, dd, J=2.0, 4.0 Hz), 9.09 (1H, s), 8.69 (1H, dd, J=2.0, 8.3 Hz), 7.78 (1H, dd, J=4.2, 8.1 Hz).

INTERMEDIATE 33

1H-Pyrrolo[2,3-c][1,8]-naphthyridin-1,3(2H)-dione

Intermediate 32 (643 mg) and urea (529 mg) were combined and heated at 170° for 45 min. The mixture was cooled and triturated with water (30 mL) and the resulting solid collected by filtration and dried to yield the title compound (507 mg) as a tan solid. M.p.>250°. NMR (DMSO-d6)δ 11.21 (1H, bs), 8.43 (1H, bd), 8.19 (1H, s), 7.92 (1H, dd), 7.01 (1H, dd).

INTERMEDIATE 34

4-Methoxy-1H-benz[f]isoindole-1,3-(2H)-dione (215 mg)

Prepared as described in Intermediate 33 from 4-methoxynaphtho[2,3-c]furan-1,3-dione (229 mg) and urea (120 mg). M.p. 216°–220°. NMR (DMSO-d6) δ 10.6 (1H, s), 7.52 (1H, d), 7.39 (1H, d), 7.34 (1H, s), 6.92 (2H, m), 3.43 (3H, s).

INTERMEDIATE 35

2-Methoxy-6-(dimethoxymethyl)benzaldehyde

A solution of the dimethyl acetal of m-anisaldehyde (490 mg) in dry diethyl ether (10 mL) at 0° was treated with a 1.7 molar solution of t-butyllithium (1.75 mL). The solution was stirred for 1 h at 0°, followed by addition of anhydrous dimethylformamide (0.25 mL). The solution was allowed to warm to 23° over 15 h, quenched by the addition of water, and extracted with ethyl acetate (2×50 mL). The combined organic layers were dried (MgSO4) and evaporated. The residue was purified by chromatography on silica using 90% hexane-ethyl acetate as eluent to afford the title compound as a pale yellow oil (255 mg).

NMR (CDCl$_3$) δ 10.60 (1H, s), 7.53 (1H, t, J=8.1 Hz), 7.38 (1H, t, J=7.2 Hz), 6.99 (1H, d, J=7.5), 6.05 (1H, s), 3.91 (3H, s), 3.42 (6H, s).

INTERMEDIATE 36

6-Methoxy-2-(dimethoxymethyl)benzenemethanol

A solution of Intermediate 35 (5.7 g) in methanol (50 mL) was treated with a solution of sodium borohydride (2.1 g) in methanol (40 mL). The reaction mixture was stirred for 4 h, then quenched by the addition of water, and extracted with chloroform (3×100 mL). The combined organic layers were dried (MgS0$_4$) and evaporated. The residue was purified by chromatography on silica using 80% hexane-ethyl acetate as eluent to afford the title compound as an oil (2.98 g).

NMR (CDCl$_3$) δ 7.27 (1H, m), 7.14 (1H, d, J=7.5 Hz), 6.92 (1H, d, J=7.8), 5.51 (1H, s), 4.81 (2H, bd), 3.87 (3H, s), 3.37 (6H, s).

INTERMEDIATE 37

1,4-Dihydro-5-methoxy-1,4-epoxynaphthalene-2,3-dicarboxylic acid, dimethyl ester A solution of Intermediate 36 (1.17 g) in dimethyl acetylenedicarboxylate (8 mL) was treated with glacial acetic acid (0.5 mL). The reaction mixture was heated to 135° for 45 min, then the excess reactants were distilled off. The residue was chromatographed on silica using 70% hexane-ethyl acetate as eluent to afford the title compound (820 mg) as an oil.

NMR (CDCl$_3$) δ 7.07 (2H, m), 6.67 (1H, dd, J=1.5, 7.5 Hz), 6.20 (1H, d, J=0.9 Hz), 5.93 (1H, d, J=1.2 Hz), 3.87 (3H, s), 3.81 (3H, s), 3.79 (3H, s).

INTERMEDIATE 38

1,2,3,4-Tetrahydro-5-methoxy-1,4-epoxynaphthalene-2,3-dicarboxylic acid, dimethyl ester A solution of Intermediate 37 (464 mg) in ethyl acetate (6 mL) was treated with 10% palladium on carbon (35 mg) and stirred under a hydrogen atmosphere for 15 h. The catalyst was removed by filtration, and the solvent evaporated to afford the title compound (455 mg) as a clear oil. NMR (CDCl$_3$) δ7.19 (1H, m), 7.02 (1H, d, J=7.2 Hz), 6.75 (1H, d, J=8.4), 5.71 (1H, m), 5.48 (1H, m), 3.84 (3H, s), 3.62 (2H, m), 3.50 (3H, s), 3.49 (3H, s).

INTERMEDIATE 39

5-Methoxy-2,3-naphthalenedicarboxylic acid, dimethyl ester

A solution of Intermediate 38 (455 mg) in toluene (10 mL) was treated with p-toluenesulfonic acid (20 mg), and heated to reflux for 4 h. The solvent was evaporated, and the residue was purified by chromatography on silica using 80% hexane-ethyl acetate as eluent to afford the title compound (370 mg) as a clear oil. NMR (CDCl$_3$) δ8.69 (1H, s), 8.15 (1H, s), 7.49 (2H, m), 6.91 (1H, dd, J=0.96, 7.4 Hz), 4.00 (3H, s), 3.95 (6H, s).

INTERMEDIATE 40

5-Methoxy-2,3-naphthalenedicarboxylic acid

A solution of Intermediate 39 in methanol (3 mL) and water (10 mL) was treated with sodium hydroxide (166 mg) at 65° for 3 h. The solution was allowed to cool, and the solvent was evaporated. The aqueous solution was diluted with water, and acidified with concentrated hydrochloric acid. The pale yellow precipitate was collected by filtration, washed with water, and dried to yield the title compound (300 mg). M.p. 210°-212° . NMR (DMSO-d6) δ8.48 (1H, s), 8.20 (1H,s), 7.62 (2H, m), 7.13 (1H, dd, J=2.0, 6.8 Hz), 4.00 (3H, s).

INTERMEDIATE 41

5-Methoxy-1H-benz[f]isoindole-1,3-(2H)-dione (237 mg)

Prepared as described in the Intermediate 33 process from Intermediate 40 (270 mg). M.p.>250°. NMR (DMSO-d6) δ11.51 (1H, s), 8.47 (1H, s), 8.40 (1H, s), 7.79 (1H, d, J=8.1 Hz), 7.69 (1H, t, J=7.8 Hz), 7.24 (1H, d, J=7.6 Hz), 4.03 (3H, s).

INTERMEDIATE 42

5-Methoxy-2-(dimethoxymethyl)benzaldehyde

A solution of the dimethyl acetal of p-anisaldehyde (5.3 g) in dry diethyl ether (90 mL) at 0° was treated with a 1.7 molar solution of t-butyl lithium (20.5 mL). The solution was stirred for 1.5 h at 0°, followed by addition of anhydrous dimethylformamide (2.9 mL). The solution was allowed to warm to 23° over 1 h, quenched by the addition of water, and extracted with ethyl acetate (2×200 mL). The combined organic layers were dried (MgSO4) and evaporated. The residue was purified by chromatography on silica using 90% hexane-ethyl acetate as eluent to afford the title compound as a pale yellow oil (2.63 g).

NMR (CDCl$_3$) δ10.45 (1H, s) 7.29 (1H, d, J=8.7 Hz), 6.97 (1H, dd, J=2.4, 8.5 Hz), 6.88 (1H, d, J=2.1 Hz), 6.02 (1H, d, J=2.2 Hz), 3.83 (3H, s), 3.44 (3H, s), 3.42 (3H, s).

INTERMEDIATE 43

5-Methoxy-2-(dimethoxymethyl)benzenemethanol

A solution of Intermediate 42 (2.6 g) in (45 mL) was treated with sodium borohydride (2 g). The reaction mixture was stirred for 2 h, then quenched by the addition of water, and extracted with chloroform (3×100 mL). The combined organic layers were dried (MgSO4) and evaporated. The residue was purified by chromatography on silica using 80% hexane-ethyl acetate as eluent to afford the title compound as an oil (1.36 g).

NMR (CDCl$_3$) δ7.28 (1H, d, J=8.1 Hz), 6.87 (1H, dd, J=2.4, 8.4 Hz), 6.77 (1H, d, J=1.8 Hz), 6.13 (1H, d, J=2.2 Hz), 5.17 (1H, m), 4.99 (1H, m), 3.82 (3H), s), 3.41 (6H, s).

INTERMEDIATE 44

3a,4,9,9a-Tetrahydro-6-methoxy-4,9-epoxynaphtho[2,3-c]furan-1,3-dione

A solution of Intermediate 43 (844 mg) and maleic anhydride (1.18 g) in methylene chloride (10 mL) was treated with acetic acid (0.2 mL) and acetic anhydride (0.1 mL) and heated to reflux for 16 h. The reaction mixture was allowed to cool, and treated with saturated aqueous sodium bicarbonate. The aqueous layer was extracted with chloroform (1×75 mL), and the combined organic layers were dried (Na$_2$SO$_4$) and evaporated. The residue was purified by chromatography on silica using 70% hexane-ethyl acetate as eluent to afford the title compound (800 mg) as a clear oil.

NMR (CDCl$_3$) δ 7.22 (1H, m), 6.90 (1H, m), 6.76 (1H, m), 5.75 (2H, m), 3.98 (1.4H, m), 3.76 (3H, m), 3.23 (0.6H, s).

INTERMEDIATE 45

6-Methoxy-naphtho[2,3-c]furan-1,3-dione

A solution of Intermediate 44 (241 mg) in toluene (5 mL) was treated with p-toluenesulfonic acid (20 mg), and heated to reflux for 4.5 h. The solvent was evaporated, and the residue dissolved in ethyl acetate. The solution was washed with saturated aqueous sodium bicarbonate, brine, dried (MgSO$_4$), and evaporated to give a brown solid. The solid was triturated with cold ethyl acetate, and the desired undissolved material was obtained by filtration. The solvent was evaporated from the filtrate, and the brown solid residue was again treated with cold ethyl acetate. The pale tan solid was filtered off and combined with the previous crop to give the title compound (211 mg). M.p. 238°-240°.

NMR (DMSO-d6) δ 8.43 (1H, s), 8.33 (1H, s), 8.00 (1H, d), 7.52 (1H, s), 7.25 (1H, d), 3.69 (3H, s).

INTERMEDIATE 46

6-Methoxy-1H-benz[f]isoindole-1,3-(2H)-dione (134 mg)

Prepared as described in the Intermediate 33 process from Intermediate 45 (159 mg) and urea (84 mg). M.p. >250°.

NMR (DMSO-d6) δ 8.36 (1H, s), 8.30 (1H, s), 8.15 (1H, d, J=9 Hz), 7.69 (1H, m), 7.39 (1H, dd, J=2.7, 9 Hz), 3.92 (3H, s).

INTERMEDIATE 47

N-[1-(R)-((1,1-Dimethylethoxy)carbonyl)-3-(1,3-dihydro-1,3-dioxo-2H-benz[f]isoindol-2-yl)propyl]-L-leucvl-N-methyl-L-phenylalanine methyl ester A mixture of Intermediate 29 (500 mg), L-phenylalanine methyl ester (210 mg), 1-hydroxybenzotriazole hydrate (100 mg) and dicyclohexylcarbodiimide (242 mg) in methylene chloride (20 mL) was stirred at 23° for 18 h. The mixture was filtered through celite and the solvent evaporated. The residue was purified by chromatography on silica gel using 10% ethyl acetate-dichloromethane as eluent to afford the title compound as a white foam (516 mg).

NMR (CDCl$_3$) δ 8.30 (2H, s), 8.03 (2H, m), 7.68 (2H, m), 7.36 (1H, br d), 7.30-7.10 (6H, m), 4.83 (1H, q), 3.90-3.70 (2H, m), 3.68 (3H, s), 3.32-3.22 (2H, m), 3.18 (1H, A part of ABX system, Jab=14.0 Hz, Jax=5.6 Hz), 3.00 (1H, B part of ABX system, Jab=13.8 Hz, Jbx=7.9 Hz), 2.00-1.80 (2H, m), 1.75-1.60 (2H, m), 1.44 (9H, s), 1.40-1.25 (2H, m), 0.83 (6H, dd).

INTERMEDIATE 48

N-[1-(R)-((1,1-Dimethylethoxy)carbonyl)-3-(1,3-dihydro-1,3-dioxo-2H-benz[f]isoindol-2-yl)propyl]-L-leucvl-N-methyl-L-phenylalanine A solution of Intermediate 47 (512 mg) in methanol (5 mL) was treated with 2N aqueous sodium hydroxide (0.65 mL) and stirred at 23° for 5 h. The solvent was removed by evaporation and the residue was treated with water (10 mL) and extracted with ethyl acetate. The aqueous layer was acidified to pH2 and extracted with ethyl acetate. The combined organic layers were dried (MgSO$_4$) and evaporated to afford the title compound as a tan solid (260 mg).

NMR (CD$_3$OD) δ 8.31 (1H, s), 7.88 (3H, m), 7.42 (2H, m), 7.00 (7H, m), 4.58 (1H, dd, J=4.6 Hz, J'=10.0 Hz), 3.48 (1H, t), 3.30 (1H, m), 3.15 (2H, m), 2.78 (1H, dd, J=10.3 Hz, J'=14.2 Hz,), 1.80 (2H, m), 1.45 (2H, m), 1.30 (9H, s), 0.68 (6H, dd).

INTERMEDIATE 49

N-[1-(R)-((1,1-Dimethylethoxy)carbonyl)-3-[bis(-phenylmethoxycarbonyl)amino]propyl]-L-leucyl-N-methyl-L-phenylalaninamide A solution of Intermediate 11(8.15 g), bis(phenylmethoxycarbonyl)ammonia (1.07 g) and triphenylphosphine (0.750 g) in dry tetrahydrofuran (10 mL) was treated with diethylazodicarboxylate (0.45 mL) at −5°. After stirring for 16 h at 23° the solvent was evaporated and the residue purified by chromatography on silica using 45% ethyl acetate-hexane as eluent to afford the title compound as a white solid (710 mg). M.p.=95°-99°.

NMR (CD$_3$OD) δ 7.65 (2H, m), 7.34 (8H, m), 7.20 (5H, m), 5.24 (4H, s), 4.57 (1H, m), 3.74 (2H, m), 3.05 (4H, m), 2.70 (3H, s), 1.84 (2H, m), 1.54 (1H, m), 1.39 (9H, s), 1.23 (2H, m), 0.82 (6H, dd).

INTERMEDIATE 50

N-[1-(R)-((1,1-Dimethylethoxy)carbonyl)-3-aminopropyl]-L-leucvl-N-methyl-L-phenylalaninamide A solution of Intermediate 49 (580 mg) in methanol (40 mL) containing 60 mg of 10% Pd/C was stirred in a hydrogen atmosphere. After stirring for 3 h, an additional 60 mg of 10% Pd/C were added and stirring was continued for 16 h. The catalyst was removed by filtration through celite and the solvent evaporated to give the title compound as a white semisolid (277 mg).

NMR (CD$_3$OD) δ 7.63 (2H, m), 7.23 (3H, m), 4.59 (1H, m), 3.24-2.98 (5H, m), 2.70 (5H, m), 1.79-1.56 (2H, m), 1.45 (9H, s), 1.26 (2H, m), 0.86 (6H, dd).

INTERMEDIATE 51

N-[4-Methylpentanoyl]-N'-methyl-L-phenylalaninamide

A solution of 4-methyl-2-oxopentanoic acid (1.7 g) and N-methyl-L-phenylalaninamide (1.99 g) in dichloromethane (100 mL) was treated with 1-hydroxybenzotriazole hydrate (1.66 g) and dicyclohexylcarbodiimide (6.2 mL of a 2M solution in dichloromethane). The reaction mixture was stirred at 23° for 17 h, filtered through celite, and concentrated. The residue was taken up in ethyl acetate and washed with 2N hydrochloric acid (2×75 mL), brine (75 mL), 5% aqueous sodium bicarbonate (2×75 mL), and brine (1×100 mL). The organic layer was dried (MgSO$_4$) and evaporated to afford a yellow solid, which was recrystallized from ethyl acetate-hexane to afford the title compound as a white solid (2.18 g). M.p. 116°–118°.

NMR (CDCl$_3$) δ 7.64 (1H, bd), 7.29 (5H, m), 6.02 (1H, m), 4.55 (1H, m), 3.11 (2H, d, J=7.3 Hz), 2.77 (3H, d, J=4.88 Hz), 2.12 (1H, m), 2.06 (2H, m), 0.96 (6H, m).

INTERMEDIATE 52

2-(S)-Amino-4-(1,3-dihydro-1,3-dioxo-2H-isoindol-2-yl)butanoic acid, ethyl ester A solution of 2-(S)-Amino-4-(1,3-dihydro-1,3-dioxo-2H-isoindol-2-yl)butanoic acid (2 g) and concentrated sulphuric acid (0.5 mL) in absolute ethanol (30 mL) was heated under reflux for 15 h. The solvent was evaporated and the residue was treated with saturated sodium bicarbonate solution and extracted with ethyl acetate. The combined organic layers were dried (MgSO$_4$) and evaporated. The residue was purified by chromatography using 20% ethyl acetate-dichloromethane then 75% ethyl acetate-dichloromethane as eluent to afford the title compound as a white solid (473 mg).

NMR (CDCl$_3$) δ 7.84 (2H, m), 7.70 (2H, m), 4.10 (2H, q, J=7.2 Hz), 3.87 (2H, m), 3.45 (1H, dd, J=4.4 Hz, J'=8.8 Hz), 2.16 (1H, m), 1.88 (1H, m), 1.68 (2H, br s), 1.23 (3H, t, J=7.1 Hz).

INTERMEDIATE 53

6H-1,4-Dioxino[2,3-f]isoindole-6,8(7H)-dione

A mixture of 1,4-benzodioxan-6,7-dicarboxylic acid (100 mg) and urea (54 mg) was heated to 160° for 2 h. When cool, the mixture was diluted with water and the resulting solid collected by filtration and washed with water and dried to afford the title compound (80 mg). M.p. 277°–280°.

EXAMPLE 1

N-[1-(R)-Carboxy-3-(1,3-dihydro-1,3-dioxo-2H-isoindol-2-yl)propyl]-L-leucyl-N-methyl-L-phenylalaninamide, trifluoroacetate (a) N-[1-(R)-((1,1-Dimethylethoxy)carbonyl-3-(1,3-dihydro-1,3-dioxo-2H-isoindol-2-yl)propyl]-L-leucyl-N-methyl-L-phenylalaninamide Diethylazodicarboxylate (0.033 mL) was added to a stirred solution of Intermediate 11 (86 mg), triphenylphosphine (55 mg) and 1,3-dihydro-1,3-dioxo-2H-isoindole (32 mg) in dry tetrahydrofuran at 5° and the resulting mixture was stirred at 21° for 16 h before concentrating in vacuo. The residue was purified by silica chromatography using methylene chloride-acetone (9:1) as eluent to give the title compound as a white foam (109 mg).

NMR (CDCl$_3$) δ 7.0–7.9 (11H, m), 4.72 (1H, m), 3.72 (2H, m), 3.34 (2H, m), 3.15 (1H, dd, J=13, 9 Hz), 2.96 (1H, dd, J=9, 4 Hz), 2.70 (3H, d, J=5 Hz), 2.04 (2H, m), 1.38 (9H, s), 1.0–1.6 (3H, m), 0.84 (6H, d, J=6 Hz).

Time of flight MS; m/e found: 580.4 (MH$^+$)

(b) N-[1-(R)-Carboxy-3-(1,3-dihydro-1,3-dioxo-2H-isoindol-2-yl)propyl]-L-leucyl-N-methyl-L-phenylalaninamide, trifluoroacetate A solution of the product of part (a) (120 mg) in trifluoroacetic acid (1 mL) was stirred for 10 min under nitrogen before concentrating in vacuo. The residue was purified by preparative reversed phase HPLC to give the title compound (16.3 mg) as a white solid.

NMR (DMSO-d$_6$) δ 8.75 (1H, broad), 8.00 (1H, q, J=5 Hz), 7.88 (4H, m), ca7.20(5H, m), 4.57 (1H, q, J=7 Hz), 3.2–3.9 (4H, m), 2.96 (1H, dd, J=13,6 Hz), 2.71 (1H, dd, J=13,6 Hz), 2.54 (3H, d, J=5 Hz), 2.00 (2H, m), 1.47 (3H, m), 0.86 (3H, d, J=7 Hz), 0.82 (3H, d, J=7 Hz). Thermospray MS; m/e found: 523 (MH$^+$).

EXAMPLE 2

N-[1-(R)-Carboxy-3-(1,3-dihydro-5-nitro-1,3-dioxo-2H-isoindol-2-yl)propyl]-L-leucyl-N-methyl-L-phenylalaninamide, trifluoroacetate (a) N-[1-(R)-((1,1-Dimethylethoxy)carbonyl)-3-(1,3-dihydro-5-nitro-1,3-dioxo-2H-isoindol-2-yl)propyl]-L-leucyl-N-methyl-L-phenylalaninamide (0.226 g)

Prepared as described for Example 1, Step (a) using 1,3-dihydro-5-nitro-1,3-dioxo-2H-isoindole.

NMR (CDCl$_3$) δ 8.65 (2H, m), 8.04 (1H, d, J=8 Hz), 7.52 (1H, d, J=8 Hz), 7.20 (5H, m), 6.78 (1H, br m), 4.68 (1H, m), 3.77 (2H, m), 3.03–3.4 (4H, m), 2.75 (3H, d, J=5 Hz), 2.03 (2H, m), 1.42 (9H, s), 1.0–1.6 (3H, m), 0.86 (6H, m).

(b) N-[1-(R)-Carboxy-3-(1,3-dihydro-5-nitro-1,3-dioxo-2H-isoindol-2-yl)propyl]-L-leucyl-N-methyl-L-phenylalaninamide, trifluoroacetate (0.243 g)

Prepared as described for Example 1, Step (b) by hydrolysis of the above product of part (a) above.

NMR (DMSO-d$_6$) δ 8.94 (1H, d, J=8 Hz), 8.63 (1H, dd, J=8 Hz), 8.49 (1H, d, J=2 Hz), 8.13 (1H, d, J=8 Hz), 8.03 (1H, q, J=5 Hz), 7.20 (5H, m), 4.58 (1H, q, J=5 Hz), 3.6–3.9 (3H, m), 3.43 (1H, t, J=5 Hz), 2.94 (1H, dd, J=13,6 Hz), 2.78 (1H, dd, J=13,9 Hz), ca2.50 (3H, obscured by DMSO), 2.08 (2H, m), 1.4–1.6 (3H, m), 0.87 (3H, d, J=6 Hz), 0.83 (3H, d, J=6 Hz).

High resolution MS; m/e Found: 568.2345 (MH$^+$). C$_{28}$H$_{34}$N$_5$O$_8$ requires 568.2408.

EXAMPLE 3

N-[1-(R)-Carboxy-3-[1,3-dihydro-5-(1,1-dimethylethyl)1,3-dioxo-2H-isoindol-2-yl]-L-leucyl-N-methyl-L-phenylalaninamide, trifluoroacetate (a) N-[1-(R)-((1,1-Dimethylethoxy)carbonyl)-3-[1,3-dihydro-5-(1,1-dimethylethyl)1,3-dioxo-2H-isoindol-2-yl]propyl]-L-leucyl-N-methyl-L-phenylalaninamide Prepared as described for Example 1, Step (a) using 1,3-dihydro-5(1,1-dimethylethyl)-1,3-dioxo-2H-isoindole.

NMR (CDCl$_3$) δ 8.30 (1H, d), 7.90 (1H, s), 7.80 (1H, s), 7.10–7.40 (8H, m), 4.85 (1H, q), 3.70–3.90 (2H, m), 3.55 (1H, t), 3.30 (1H, dd), 3.00–3.20 (2H, m), 2.80 (3H, d), 2.20–2.40 (2H, m), 1.75 (1H, m), 1.40–1.60 (2H, m), 1.4 (18H, s), 0.85 (6H, m).

Fast atom bombardment MS; m/e found: 635 (MH$^+$).

(b) N-[1-(R)-Carboxy-3-[1,3-dihydro-5-(1,1-dimethylethyl)1,3-dioxo-2H-isoindol-2-yl]-L-leucyl-N-methyl-L-phenylalaninamide, trifluoroacetate Prepared as described for Example 1, Step (b) by hydrolysis of the product of part (a) above. Mp 165°–7°.

NMR (CDCl$_3$) δ 8.70 (1H, d), 7.1–7.4 (8H, m), 4.8–5.4 (3H, broad), 4.8 (1H, q), 4.1 (1H, t), 3.7–3.9 (2H, m), 3.5 (1H, brs), 3.2–3.3 (1H, dd), 3.0 (2H, m), 2.8 (3H, d), 2.4–2.6 (2H, m), 1.9–2.1 (1H, m), 1.65 (1H, t), 1.5 (9H, s), 0.9 (6H, d).

Accurate mass; m/e found: 579.3175 (MH$^+$). C$_{32}$H$_{43}$N$_4$O$_6$ requires: 579.3171.

EXAMPLE 4

N-[1-(R)-Carboxy-3-(1,3-dihydro-1,3-dioxo-2H-isoindol-2-yl)propyl]-L-leucyl-N-methyl-3-(2-naphthalenyl)-L-alaninamide, trifluoroacetate (a) N-[1-(R)-((1,1-Dimethylethoxy)carbonyl)-3-(1,3-dihydro-1,3-dioxo-2H-isoindol-2-yl)propyl]-L-leucyl-N-methyl-3-(2-naphthalenyl)-L-alaninamide (0.103 g)

Prepared as described for Example 1, Step (a) using Intermediate 15 (0.235 g).

(b) N-[1-(R)-Carboxy-3-(1,3-dihydro-1,3-dioxo-2H-isoindol-2-yl)propyl]-L-leucyl-N-methyl-3-(2-naphthalenyl)-L-alaninamide, trifluoroacetate (53 mg)

Prepared as described for Example 1, Step (b) using the product of part (a) above.

NMR (DMSO-$d_6$) δ 8.80 (1H, broad), 8.00 (1H, m), 7.3–7.9 (9H, m), 4.64 (1H, q, J=7 Hz), 2.5–3.9 (9H, m), 1.92 (2H, m), 1.3–1.6 (3H, m), 0.82 (3H, d, J=6 Hz), 0.76 (3H, d, J=6 Hz).

EXAMPLE 5

N-[1-(R)-Carboxy-3-(1,3-dihydro-1,3-dioxo-2H-isoindol-2-yl)propyl]-L-leucyl-N-methyl-L-tryptophanamide, trifluoroacetate (a) N-[1-(R)-((1,1-Dimethylethoxy)carbonyl)-3-(1,3-dihydro-1,3-dioxo-2H-isoindol-2-yl)propyl]-L-leucyl-N-methyl-L-tryptophanamide (130 mg)

Prepared as described for Example 1, Step (a) using Intermediate 17 (0.162 g).

[α]$_D$ −3.7° (c=0.54, MeOH).

NMR (CDCl$_3$) δ 7.94 (1H, d, J=8 Hz), 7.0–7.9 (10H, m), 4.76 (1H, m), 3.2–3.6 (5H, m), 2.91 (1H, m), 2.70 (3H, d, J=5 Hz), 1.89 (2H, m), 1.0–1.6 (3H, m), 1.37 (9H, s), 0.83 (6H, d, J=6 Hz).

(b) N-[1-(R)-Carboxy-3-(1,3-dihydro-1,3-dioxo-2H-isoindol-2-yl)propyl]-L-leucyl-N-methyl-L-tryptophanamide, trifluoroacetate (57 mg)

Prepared as described for Example 1, Step (b) using the product of part (a) above.

NMR (DMSO-$d_6$) δ 10.84 (1H, broad s), 8.87 (1H, broad d, J=6 Hz), 7.98 (1H, q, J=5 Hz), 7.84 (4H, m), 7.60 (1H, d, J=8 Hz), 7.31 (1H, d, J=8 Hz), 7.13 (1H, d, J=2 Hz), 7.04 (1H, t, J=7 Hz), 6.94 (1H, t, J=5 Hz), 4.58 (1H, q, J=7 Hz), 3.6–3.9 (3H, m), 3.48 (1H, m), 3.01 (1H, dd, J=13,6 Hz), 2.95 (1H, dd, J= 13,8 Hz), ca2.50 (3H, obscured by DMSO), 2.06 (2H, m), 1.55 (3H, m), 0.87 (3H, d, J=6 Hz), 0.84 (3H, d, J=6 Hz).

Fast atom bombardment MS; m/e found: 562 (MH$^{30}$).

EXAMPLE 6

N-[1-(R)-Carboxy-3-(5-acetylamino-2,3-dihydro-1,3-dioxo-1H-isoindol-2-yl)propyl]-L-leucyl-N-methyl-L-phenylalaninamide, trifluoroacetate (a) N-[1-(R)-((1,1-Dimethylethoxy)carbonyl)-3-(5-acetylamino-2,3-dihydro-1,3-dioxo-1H-isoindol-2-yl)propyl]-L-leucyl-N-methyl-L-phenylalaninamide, trifluoroacetate (40 mg)

Prepared as described for Example 1, Step (a) using Intermediate 20 (61 mg).

NMR (CD$_3$OD) δ 8.18 (1H, s), 7.70 (2H, s), 7.13 (5H, m), 4.64 (1H, m), 3.75 (1H, m), 3.60 (1H, m), 3.44 (2H, m), 2.76–3.00 (2H, m), 2.56 (3H, s), 2.09 (3H, s), 1.92 (1H, m), 1.70 (1H, m), 1.61 (2H, m), 1.45 (9H, s), 1.19 (1H, m), 0.91 (3H, d, J=5.1 Hz), 0.85 (3H, d, J=4.9 Hz).

(b) N-[1-(R)-Carboxy-3-(5-acetylamino-2,3-dihydro-1,3-dioxo-1H-isoindol-2-yl)propyl]-L-leucyl-N-methyl-L-phenylalaninamide, trifluoroacetate (10 mg)

Prepared as described in Example 1, Step (b) using the product of part (a) above. M.p. 216°–220°.

NMR (CD$_3$OD) δ 8.14 (1H, s), 7.70 (2H, m), 7.15 (5H, m), 4.55 (1H, m), 3.62 (3H, m), 3.49 (1H, m), 2.84–3.15 (2H, m), 2.54 (3H, s), 2.08 (3H, s), 1.96 (2H, m), 1.58 (3H, m), 0.87 (3H, d, J=6.0), 0.83 (3H, d, J=6.0).

High resolution mass spectrometry; m/e found: 580-2756(MH+); C$_{30}$H$_{38}$N$_5$O$_7$ requires: 580.2771.

EXAMPLE 7

N-[1-(R)-Carboxy-3-(2,3-dihydro-5-morpholino-1,3-dioxo-1H-isoindol-2-yl)propyl]-L-leucyl-N-methyl-L-phenylalaninamide, trifluoroacetate (a) N-[1-(R)-((1,1-Dimethylethoxy)carbonyl)-3-(2,3-dihydro-5-morpholino-1,3-dioxo-1H-isoindol-2-yl)propyl]-L-leucyl-N-methyl-L-phenylalaninamide, trifluoroacetate (80 mg).

Prepared as described in Example 1, Step (a) using Intermediate 23 (51 mg).

NMR (CD$_3$OD) δ 7.51 (1H, d, J=8.7 Hz), 7.16 (1H, d, J=2.0 Hz), 7.04 (6H, m), 4.56 (2H, m), 3.71 (1H, m), 3.64 (4H, m), 3.50 (1H, m), 3.36 (1H, m), 3.18 (4H, m), 2.67–2.93 (2H, m), 2.48 (3H, s), 1.78 (2H, m), 1.62 (1H, m), 1.50 (2H, m), 0.83 (3H, d, J=5.6 Hz), 0.77 (3H, d, J=5.9 Hz).

(b) N-[1-(R)-Carboxy-3-(2,3-dihydro-5-morpholino-1,3-dioxo-1H-isoindol-2-yl)propyl]-L-leucyl-N-methyl-L-phenylalaninamide, trifluoroacetate (58 mg)

Prepared as described in Example 1, Step (b) using the product of part (a) above. M.p. 118°–122°.

NMR (CD$_3$OD) δ 7.59 (1H, d, J=8.4 Hz), 7.25 (1H, d, J=2.2), 7.13 (6H, m), 4.57 (1H, m), 3.73 (4H, m), 3.68 (1H, t, J=6.1 Hz), 3.59 (2H, m), 3.52 (1H, m), 3.28 (4H, m), 2.82–3.04 (2H, m), 2.54 (3H, s), 1.93 (2H, m), 1.58 (3H, m), 0.88 (3H, d, J=5.9 Hz), 0.84 (3H, d, J=5.9 Hz).

High resolution mass spectrometry; m/e found: 608.3063(MH+); C$_{32}$H$_{42}$N$_5$O$_7$ requires: 608.3084.

EXAMPLE 8

N-[1-(R)-Carboxy-3-(5,7-dihydro-5,7-dioxo-6H-pyrrolo[3,4-b]pyrid-2yl)propyl]-L-leucyl-N-methyl-L-phenylalaninamide, trifluoroacetate (a) N-[1-(R)-((1,1-Dimethylethoxy)carbonyl)-3-(5,7-dihydro-5,7-dioxo-6H-pyrrolo[3,4-b]pyrid-2yl)propyl]-L-leucyl-N-methyl-L-phenylalaninamide (34 mg)

Prepared as described in Example 1, Step (a) using 5H-pyrrolo[3,4-b]pyridine-5,7(6H)-dione (26 mg).

NMR (CDCl$_3$) δ 9.0–8.8 (br s, 1H), 8.4–7.8 (br m, 5H), 7.2 (m, 5H), 4.8 (m, 1H), 3.9–3.7 (br m, 2H), 3.6 (m, 1H), 3.2 (m, 1H), 3.0 (m, 1H), 2.8 (d, 3H), 2.2 (m, 2H), 1.8–1.6 (br m, 4H), 1.4 (s, 9H), 0.9 (d, 6H).

(b) N-[1-(R)-Carboxy-3-(5,7-dihydro-5,7-dioxo-6H-pyrrolo[3,4-b]pyrid-2yl)propyl]-L-leucyl-N-methyl-L-phenylalaninamide, trifluoroacetate (27.2 mg)

Prepared as described in Example 1, Step (b) using the product of part (a) above. M.p. 106°–110°.

NMR (DMSO-$d_6$) δ 8.90–8.80 (1H, m), 8.60 (1H, m), 8.20 (1H, m), 8.00–7.60 (4H, m), 7.20 (5H, br s), 4.50 (1H, m), 4.00 (1H, m), 2.80 (3H, d), 2.60 (2H, m), 1.80 (4H, m), 1.50 (2H, m), 1.10 (2H, m), 0.90 (6H, d).

High resolution mass spectrometry; m/e found: 524.2490(MH+); C$_{27}$H$_{34}$N$_5$O$_6$ requires: 524.2509.

EXAMPLE 9

N-[1-(R)-Carboxy-3-(1,3-dihydro-1,3-dioxo-2Hpyrrolo[3,4-c]pyrid-2yl)propyl]-L-leucyl-N-methyl-L-phenylalaninamide, trifluoroacetate (a) N-[1-(R)-((1,1-Dimethylethoxy)carbonyl)-3-(1,3-dihydro-1,3-dioxo-2H-pyrrolo[3,4-c]pyrid-2yl)propyl]-L-leucyl-N-methyl-L-phenylalaninamide (56 mg)

Prepared as described in Example 1, Step (a) using 1H-pyrrolo[3,4-c]pyridine-1,3(2H)-dione (93 mg).

NMR (CDCl$_3$) δ 9.2 (s, 1H), 9.15 (d, 1H), 7.8 (d, 1H), 7.7 (m, 1H), 7.6 (m, 1H), 7.3 (m, 5H), 7.0 (m, 1H), 4.7 (m, 1H), 3.8 (t, 2H), 3.4 (m, 2H), 3.2 (t, 2H), 3.0 (q, 1H), 2.8 (d, 3H), 2.1 (m, 2H), 1.8 (m, 2H), 1.6 (m, 1H), 1.4 (s, 9H), 0.9 (d, 6H).

(b) N-[1-(R)-Carboxy-3-(1,3-dihydro-1,3-dioxo-2Hpyrrolo[3,4-c]pyrid-2yl)propyl]-L-leucyl-N-methyl-L-phenylalaninamide, trifluoroacetate (29.2 mgt)

Prepared as described in Example 1, Step (b) using the product of part (a) above.

NMR (CDCl$_3$) δ 9.2 (s, 1H), 9.15 (d, 1H), 7.8 (d, 1H), 7.7 (m, 1H), 7.6 (m, 1H), 7.3 (m, 5H), 7.0 (m, 1H), 4.7 (m, 1H), 3.8 (t, 2H), 3.4 (m, 2H), 3.2 (t, 2H), 3.15(q, 1H), 2.8 (d, 3H), 2.1 (m, 2H), 1.8 (m, 2H), 1.6 (m, 1H), 0.9 (d, 6H).

High Resolution Mass Spectrometry; m/e Found: 524.2505 (MH+); C$_{27}$H$_{33}$N$_5$O$_6$ requires: 524.2499.

EXAMPLE 10

Method A

N-[1-(R)-Carboxy-3-(1,3-dihydro-1,3-dioxo-2H-benz[f]isoindol-2-yl)propyl]-L-leucyl-N-methyl-L-phenylalaninamide, trifluoroacetate (a) N-[1-(R)-((1,1-Dimethylethoxy)carbonyl)-3-(1,3-dihydro-1,3-dioxo-2H-benz[f]isoindol-2-yl)propyl]-L-leucyl-N-methyl-L-phenylalaninamide.

A solution of Intermediate 11 (190 mg) in dry tetrahydrofuran (5 mL) at 0° was treated with triphenylphosphine (121 mg), 1,3-dihydro-1,3-dioxo-2H-benz[f]isoindole (91 mg) and diethylazidodicarboxylate (72 μL). The mixture was allowed to warm up to 23° over 15 h. The solvent was evaporated and the residue was purified by preparative reverse phase HPLC. Lyophilization of the appropriate fractions afforded the title compound as a white solid (133 mg).

NMR (CDCl$_3$) δ 8.35 (2H, s), 8.09 (2H, m), 7.86 (1H, d, J=8 Hz), 7.72 (2H, m), 7.28 (5H, s), 7.18 (1H, m), 4.74 (1H, m), 3.80 (2H, m), 3.36 (2H, m), 3.20 (1H, dd, J=13, 8 Hz), 2.98 (1H, m), 2.69 (3H, d, J=6 Hz), 2.10 (2H, m), 1.0–1.6 (3H, m), 1.36 (9H, s), 0.86 (6H, d, J=6 Hz).

Chemical Ionisation MS; m/e found: 629 (MH+).

(b) N-[1-(R)-Carboxy-3-(1,3-dihydro-1,3-dioxo-2H-benz[f]isoindol-2-yl)propyl]-L-leucyl-N-methyl-L-phenylalaninamide, trifluoroacetate A solution of the product of part (a) (118 mg) in trifluoroacetic acid (3 mL) was stirred at 23° for 6 h. The solvent was removed by evaporation and the residue purified by reverse phase HPLC to afford the title compound as a white solid (95 mg). M.p. 199°–200°.

NMR (DMSO-d$_6$) δ 8.94 (1H, d, J=8 Hz), 8.04 (1H, q, J=5 Hz), 8.54 (2H, s), 8.26 (2H, m), 7.80 (2H, m), 7.20 (5H, m), 4.60 (1H, q, J=6 Hz), 3.6–3.8 (3H, m), 3.43 (1H, t, J=5 Hz), 2.95 (1H, dd, J=12 Hz), 2.79 (1H, dd, J=12, 8 Hz), 2.50 (3H, obsecured by DMSO), 2.08 (2H, m), 1.4–1.6 (3H, m), 0.87 (3H, d, J=6 Hz), 0.83 (3H, d, J=6 Hz).

High Resolution MS; m/e Found: 573.2701 (MH+). C$_{32}$H$_{36}$N$_4$O$_6$ requires: 573.2722.

Method B

A solution of Intermediate 48 (100 mg), 1-hydroxybenzotriazole hydrate (20 mg), dicyclohexylcarbodiimide (40 mg) and methylamine hydrochloride (50 mg) in dimethylformamide (10 mL) was treated with triethylamine (0.5 mL) and the mixture stirred at 23° for 18 h. The solvent was removed by evaporation and the residue dissolved in methylene chloride (20 mL), filtered through celite, and washed with saturated aqueous sodium bicarbonate solution. The organic layer was dried (Na$_2$SO$_4$) and evaporated and the residue was purified by chromatography using 40% ethyl acetate-dichloromethane as eluent to afford the title compound as a white solid (67 mg).

Method C

A mixture of 2,3-naphthalic anhydride (26 mg) and Intermediate 50 (50 mg) was slowly heated to 120°. After 1 h, the melt was cooled to 23° and the mixture purified by reverse phase HPLC to give the title compound as a white powder (22 mg).

EXAMPLE 11

N-[1-(R)-Carboxy-3-(1,3-dihydro-1,3-dioxo-2H-benz[f]isoindol-2-yl)propyl]-L-leucyl-N-(morpholinoethyl)-L-leucinamide, ditrifluoroacetate (a) N-[1-(R)-((1,1-Dimethylethoxy)carbonyl)-3-(1,3-dihydro-1,3-dioxo-2H-benz[f]isoindol-2-yl)propyl]-L-leucyl-N-(morpholinoethyl)-L-leucinamide A solution of Intermediate 26 (500 mg), triphenylphosphine (280 mg) and 1,3-dihydro-1,3-dioxo-2H-benz[f]isoindole (210 mg) in dry tetrahydrofuran (20 mL) was cooled to 0° and treated with diethylazidodicarboxylate (170 μL). The mixture was allowed to warm up to 23° over 15 h. The solvent was evaporated and the residue purified by reverse phase HPLC to afford the title compound as a white solid (400 mg).

NMR (CDCl$_3$) δ 8.33 (s, 2H), 8.07 (dd, 2H), 7.72 (dd, 2H), 7.55 (d, 1H), 6.94 (m, 1H), 4.40 (m, 1H), 3.85 (m, 2H), 3.65 (m, 4H), 3.40–3.15 (m, 4H), 2.40 (m, 6H), 2.15 (m, 2H), 1.90–1.60 (m, 7H), 1.43 (s, 9H), 0.95 (m, 12H).

(b) N-[1-(R)-Carboxy-3-(1,3-dihydro-1,3-dioxo-2H-benz[f]isoindol-2-yl)propyl]-L-leucyl-N-(morpholinoethyl)-L-leucinamide, ditrifluoroacetate A solution of the product of part (a) (90 mg) in trifluoroacetic acid (5 mL) was stirred at 23° for 15 h. The solvent was evaporated and the residue purified by reverse phase HPLC to afford the title compound as a white solid (60 mg). M.p. 115°–7°.

NMR (D$_2$O) δ 7.55 (m), 7.35 (m), 4.05 (m), 3.90–3.70 (m), 3.60–3.20 (m), 3.10–2.80 (m), 1.95 (m), 1.60–1.20 (m), 0.70 (m), 0.55 (m).

Analysis Found: C, 52.30; H, 6.01; N, 7.89; F, 13.53; H$_2$O, 2.62; C$_{38}$H$_{49}$F$_6$N$_5$O$_{11}$.H$_2$O requires: C, 51.64; H, 5.82; N, 7.92; F, 12.90; H$_2$O, 2.03%.

High resolution MS; m/e Found: 638.3532 (MH+). C$_{34}$H$_{48}$N$_5$O$_7$ requires: 638.3554.

EXAMPLE 12

N-[1-(R)-Carboxy-3-(1,3-dihydro-1,3-dioxo-2H-benz[f]isoindol-2-yl)propyl]-L-leucyl-N-methyl-L-leucinamide, trifluoroacetate (a) N-[1-(R)-((1-Dimethylethoxy)carbonyl)-3-(1,3-dihydro-1,3-dioxo-2H-benz[f]isoindol-2-yl)propyl]-L-leucyl-N-methyl-L-leucinamide A mixture of Intermediate 29 (100 mg), N-methyl-L-leucinamide (31 mg) and 1-hydroxybenzotriazole hydrate (17 mg) in methylene chloride (10 mL) was treated with dicyclohexylcarbodiimide (48 mg) and the mixture stirred for 15 h at 23°. The mixture was filtered through celite and the solvent evaporated. The residue was purified by reverse phase HPLC to afford the title compound as a white foam (61 mg).

NMR (CDCl$_3$) δ 8.35 (s), 8.10 (m), 7.70 (m), 4.60-4.20 (m), 3.90 (m), 3.70 (m), 3.10 (m), 2.90-2.70 (m), 2.40-1.60 (m), 1.45 (s), 1.00 (m).

(b) N-[1-(R)-Carboxy-3-(1,3-dihydro-1,3-dioxo-2H-benz[f]isoindol-2-yl)propyl]-L-leucyl-N-methyl-L-leucinamide, trifluoroacetate A solution of the product of part (a) (40 mg) in trifluoroacetic acid (5 mL) was allowed to stand at 23° for 15 h. The solvent was evaporated and the residue purified by reverse phase HPLC to furnish the title compound as a white foam (16 mg). M.p. 115°-25°.

NMR (CD$_3$OD) δ 8.30 (2), 8.05 (m), 7.65 (m), 4.30 (m), 3.90-3.65 (m), 2.55 (s), 2.20 (m), 1.70-1.40 (m), 0.90-0.75 (m).

High resolution MS; m/e found: 539.2838 (MH+). C$_{29}$H$_{38}$N$_4$O$_6$ requires: 539.2859

EXAMPLE 13

N-[1-(R)-Carboxy-3-(1,3-dihydro-1,3-dioxo-2H-benz[f]isoindol-2-yl)propyl]-L-leucyl-N-methyl-L-methioninamide, trifluoroacetate (a) N-[1-(R)-((1,1-Dimethylethoxy)carbonyl)-3-(1,3-dihydro-1,3-dioxo-2H-benz[f]isoindol-2-yl)propyl]-L-leucyl-N-methyl-L-methioninamide (63 mg)

Prepared as described in Example 12, Step (a) using N-methyl-L-methioninamide (47 mg).

NMR (CDCl$_3$) δ 8.30 (s, 2H0, 8.20 (d,1H), 8.10 (dd, 2H), 7.70 (dd, 2H), 4.60 (m, 1H), 3.90 (m, 2H), 3.60 (t, 1H), 3.40-3.20 (m, 3H), 2.70(d, 3H), 2.55 (t, 2H), 2.40-2.30 (m, 2H), 2.10 (s, 3H), 1.80 (d, 2H), 1.70 (d, 2H), 1.40 (s, 9H), 0.9 (d, 6H).

Fast atom bombardment MS; m/e Found: 613 (MH+).

(b) N-[1-(R)-Carboxy-3-(1,3-dihydro-1,3-dioxo-2H-benz[f]isoindol-2-yl)propyl]-L-leucyl-N-methyl-L-methioninamide, trifluoroacetate (21 mg)

Prepared as described in Example 12, Step (b) by hydrolysis of the product of part (a) above (63 mg). M.p. 174°.

NMR (CD$_3$OD) δ 8.30 (s), 8.05 (m), 7.65 (m), 4.40 (m), 3.85 (m), 3.75 (m), 2.60 (s), 2.40 (m), 1.95 (s), 1.80-1.50 (m), 0.85 (m).

Fast atom bombardment MS; m/e Found: 557 (MH+).

EXAMPLE 14

N-[1-(R)-Carboxy-3-(1,3-dihydro-1,3-dioxo-2H-pyrrolo[3,4-b]quinolin-2-yl)propyl]-L-leucyl-N-methyl-L-phenylalaninamide, trifluoroacetate (a) N-[1-(R)-((1,1-Dimethylethoxy)carbonyl)-3-(1,3-dihydro-1,3-dioxo-2H-pyrrolo[3,4-b]quinolin-2-yl)propyl]-L-leucyl-N-methyl-L-phenylalaninamide (100 mg)

Prepared as described in Example 10, Step (a) using Intermediate 30 (57 mg).

NMR (CDCl$_3$) δ 8.67 (s, 1H), 8.45 (d, 1H), 8.11 (d, 1H), 7.98 (t, 1H), 7.60 (m, 5H), 4.72 (m), 3.85 (m), 3.50-3.10 (m), 2.71 (d, 3H), 2.15 (m), 1.50 (m), 1.40 (s, 9H), 1.25 (m), 0.84 (m, 6H).

(b) N-[1-(R)-Carboxy-3-(1,3-dihydro-1,3-dioxo-2H-pyrrolo[3,4-b]quinolin-2-yl)propyl]-L-leucyl-N-methyl-L-phenylalaninamide, trifluoroacetate (10 mg)

Prepared as described in Example 10, Step (b) by hydrolysis of the product of part (a) above (160 mg).

NMR (CD$_3$OD) δ 8.75 (s, 1H), 8.13 (m, 2H), 7.89 (m, 1H), 7.72 (m, 1H), 7.13 (m, 5H), 4.54 (m), 3.87 (m), 3.65 (m), 3.10-2.80 (m), 2.10 (m), 1.56 (m), 0.85 (m, 6H).

Fast atom bombardment MS; m/e Found: 574 (MH+).

EXAMPLE 15

N-[1-(R)-Carboxy-3-(1,3,5,7-tetraoxo-2H,6H-benzo[1,2-c:4,5-c']dipyrrol-2-yl)propyl]-L-leucyl-N-methyl-L-phenylalaninamide, trifluoroacetate (a) N-[1-(R)-((1,1-Dimethylethoxy)carbonyl)-3-(1,3,5,7-tetraoxo-2H,6H-benzo[1,2-c:4,5-c']dipyrrol-2-yl)propyl]-L-leucyl-N-methyl-L-phenylalaninamide (60 mg)

Prepared as described in Example 10, Step (a) using 1,3,5,7-tetraoxo-2H,6H-benzo[1,2-c:4,5-c']dipyrrole (52 mg).

NMR (CDCl$_3$) δ 8.5 (m, 1H), 8.4 (s, 2H), 8.3 (m, 1H), 7.4-7.2 (m, 6H), 6.8 (m, 1H), 4.7 (m, 1H), 4.3 (q, 1H), 3.8 (m, 1H), 3.3 (dd, 1H), 3.2-3.0 (m, 2H), 2.8 (d, 3H), 2.1 (m, 2H), 1.6 (m, 3H), 1.4 (s, 9H), 0.9 (d, 6H).

(b) N-[1-(R)-Carboxy-3-(1,3,5,7-tetraoxo-2H,6H-benzo[1,2-c:4,5-c']dipyrrol-2-yl)propyl]-L-leucyl-N-methyl-L-phenylalaninamide, trifluoroacetate (30 mg)

Prepared as described for Example 10, Step (b) by hydrolysis of the product of part (a) above (60 mg).

High resolution MS: m/e Found: 592.2372 (MH+). C$_{30}$H$_{34}$N$_5$O$_8$ requires: 592.2397.

NMR (CD$_3$OD) δ 8.1 (s, 2H), 7.0 (s, 5H), 4.6 (t, 1H), 3.6-3.8 (br m, 4H), 2.7-3.0 (m, 2H), 2.5 (s, 3H), 1.8-2.0 (br m, 2H), 1.4-1.7 (br m, 3H), 0.8-1.0 (d, 6H).

EXAMPLE 16

N-[1-(R)-Carboxy-3-(1,3-dihydro-1,3-dioxo-2H-pyrrolo[2,3-c][1,8]-naphthyridin-2-yl)propyl]-L-leucyl-N-methyl-L-phenylalaninamide, trifluoroacetate (a) N-[1-(R)-((1,1-Dimethylethoxy)carbonyl)-3-(1,3-dihydro-1,3-dioxo-2H-pyrrolo[2,3-c][1,8]-naphthyridin-2-yl)propyl]-L-leucyl-N-methyl-L-phenylalaninamide, trifluoroacetate (167 mg)

Prepared as described in Example 10, Step (a) using Intermediate 33 (112 mg).

NMR (CD$_3$OD) δ 9.19 (1H, bd), 8.88 (1H, s), 8.64 (1H, d, J=8.1 Hz), 7.76 (1H, m), 7.13 (5H, m), 4.62 (2H, m), 3.76 (3H, m), 3.53 (1H, m), 2.79-3.04 (2H, m), 2.57 (3H, s), 2.04 (2H, m), 1.60 (2H, m), 1.49 (9H, s), 0.89 (3H, d, J=5.6 Hz), 0.84 (3H, d, J=6 Hz).

(b) N-[1-(R)-Carboxy-3-(1,3-dihydro-1,3-dioxo-2H-pyrrolo[2,3-c][1,8]-naphthyridin-2-yl)propyl]-L-leucyl-N-methyl-L-phenylalaninamide, trifluoroacetate (36 mg)

Prepared as described in Example 10, Step (b) by hydrolysis of the product of part (a) above (121 mg).

NMR (CD$_3$OD) δ 9.15 (1H, br d), 8.88 (1H, s), 8.61 (1H, d, J=8.4 Hz), 7.75 (1H, dd, J=4.4, 4.2 Hz), 7.14 (5H, m), 4.64 (2H, m), 3.6–3.9 (4H, m), 2.8–3.03 (2H, m), 2.52 (3H, s), 1.9–2.1 (2H, m), 1.42–1.75 (3H, m), 0.87 (3H, d, J=5.4 Hz), 0.85 (3H, d, J=5.4 Hz).

High resolutions MS: m/e Found:575.2632 (MH+). C$_{30}$H$_{35}$N$_6$O$_6$ requires: 575.2618.

EXAMPLE 17

N-[1-(R)-Carboxy-3-(1,3-dihydro-4-methoxy-1,3-dioxo-2H-benz[f]isoindol-2-yl)propyl]-L-leucyl-N-methyl-L-phenylalaninamide, trifluoroacetate (a) N-[1-(R)-((1,1-Dimethylethoxy)carbonyl)-3-(1,3-dihydro-4-methoxy-1,3-dioxo-2H-benz[f]isoindol-2-yl)propyl]-L-leucyl-N-methyl-L-phenylalaninamide, trifluoroacetate (70 mg)

Prepared as described in Example 10, Step (a) using Intermediate 34 (73 mg). NMR (CD$_3$OD) δ8.31 (1H, m), 7.99 (1H, s), 7.63 (2H, m), 7.09 (6H, m), 4.63 (1H, m), 4.32 (3H, s), 3.60–3.80 (2H, m), 3.40–3.60 (2H, m), 2.77–3.00 (2H, m), 2.53 (3H, s), 1.88 (2H, m), 1.51–1.71 (3H, m), 1.43 (9H, s), 0.89 (3H, d, J=5.9 Hz), 0.83 (3H, d, J=6.1 Hz).

(b) N-[1-(R)-Carboxy-3-(1,3-dihydro-4-methoxy-1,3-dioxo-2H-benz[f]isoindol-2-yl)propyl]-L-leucyl-N-methyl-L-phenylalaninamide, trifluoroacetate (30 mg)

Prepared as described in Example 10, Step (b) by hydrolysis of the product of part (a) above (70 mg). NMR (CD$_3$OD) δ 8.33 (1H, m), 7.97 (1H, s), 7.63 (2H, m), 7.10 (6H, m), 4.57 (1H, m), 4.31 (3H, s), 3.77 (1H, m), 3.66 (3H, m), 2.80–3.00 (2H, m), 2.51 (3H, s), 1.95 (2H, m), 1.60 (3H, m), 0.88 (3H, d, J=5.6 Hz), 0.83 (3H, d, J=5.9 Hz).

High resolution MS: m/e found 603.2817 (MH+). C$_{33}$H$_{39}$N$_4$O$_7$ requires: 603.2821.

EXAMPLE 18

N-[1-(R)-Carboxy-3-(1,3-dihydro-5-methoxy-1,3-dioxo-2H-benz[f]isoindol-2-yl)propyl]-L-leucyl-N-methyl-L-phenylalaninamide, trifluoroacetate (a) N-[1-(R)-((1,1-Dimethylethoxy)carbonyl)-3-(1,3-dihydro-5-methoxy-1,3-dioxo-2H-benz[f]isoindol-2-yl)propyl]-L-leucyl-N-methyl-L-phenylalaninamide, trifluoroacetate (156 mg)

Prepared as described in Example 10, Step (a) using Intermediate 41 (75 mg).

NMR (CD$_3$OD) δ 8.58 (1H, s), 8.22 (1H, s), 7.57 (2H, m), 7.09 (6H, m), 4.60 (1H, m), 3.96 (3H, s), 3.67 (3H, m), 3.40 (1H, m), 2.81–2.97 (2H, m), 2.52 (3H, s), 1.9 (2H, m), 1.52 (3H, m), 1.42 (9H, s), 0.88 (3H, d, J=5.7 Hz), 0.82 (3H, d, J=5.7 Hz).

(b) N-[1-(R)-Carboxy-3-(1,3-dihydro-5-methoxy-1,3-dioxo-2H-benz[f]isoindol-2-yl)propyl]-L-leucyl-N-methyl-L-phenylalaninamide, trifluoroacetate (80 mg)

Prepared as described in Example 10, Step (b) by hydrolysis of the product of part (a) above (136 mg).

NMR (CD$_3$OD) δ 8.52 (1H, s), 8.16 (1H, s), 7.53 (2H, m), 7.08 (6H, m), 4.55 (1H, m), 3.93 (3H, s), 3.69 (3H, m), 3.57 (1H, m), 2.79–2.99 (2H, m), 2.49 (3H, s), 1.97 (2H, m), 1.59 (3H, m), 0.86 (3H, d, J=5.6 Hz), 0.81 (3H, d, J=5.9 Hz).

High resolution MS: m/e Found: 603.2808 (MH+). C$_{33}$H$_{39}$N$_4$O$_7$ requires: 603.2821.

EXAMPLE 19

N-[1-(R)-Carboxy-3-(1,3-dihydro-6-methoxy-1,3-dioxo-2H-benz[f]isoindol-2-yl)propyl]-L-leucyl-N-methyl-L-phenylalaninamide, trifluoroacetate (a) N-[1-(R)-((1,1-Dimethylethoxy)carbonyl)-3-(1,3-dihydro-6-methoxy-1,3-dioxo-2H-benz[f]isoindol-2-yl)propyl]-L-leucyl-N-methyl-L-phenylalaninamide, trifluoroacetate (30 mg)

Prepared as described in Example 10, Step (a) using Intermediate 46 (40 mg).

NMR (CD$_3$OD) δ 8.19 (1H, d, J=3.2 Hz), 7.92 (1H, d, J=9 Hz), 7.43 (1H, d, J=2.1 Hz), 7.24 (1H, dd, J=2.4, 9 Hz), 7.15 (6H, m), 4.63 (1H, m), 3.86 (3H, s), 3.60 (3H, m), 3.39 (1H, m), 2.8–3.01 (2H, m), 2.52 (3H, s), 1.92 (2H, m), 1.55 (3H, m), 1.42 (9H, s), 0.82 (6H, m).

(b) N-[1-(R)-Carboxy-3-(1,3-dihydro-6-methoxy-1,3-dioxo-2H-benz[f]isoindol-2-yl)propyl]-L-leucyl-N-methyl-L-phenylalaninamide, trifluoroacetate (19 mg)

Prepared as described in Example 10, Step (b) by hydrolysis of the product of part (a) above (28 mg).

NMR (CD$_3$OD) δ 8.16 (1H, d, J=3.9 Hz), 7.91 (1H, d, J=9 Hz), 7.41 (1H, d, J=2.7 Hz), 7.24 (1H, dd, J=2.4, 9 Hz), 7.10 (6H, m), 4.56 (1H, m), 3.86 (3H, s), 3.70 (2H, m), 3.56 (1H, m), 3.40 (1H, m), 2.81–3.02 (2H, m), 2.51 (3H, s), 1.97 (2H, m), 1.62 (3H, m), 0.87 (3H, d, J=5.9 Hz), 0.82 (3H, d, J=5.9 Hz).

High resolution MS: m/e Found: 603.2808 (MH+). C$_{33}$H$_{39}$N$_4$O$_7$ requires: 603.2817.

EXAMPLE 20

N-[1-(R)-Carboxy-3-(1,3-dihydro-1,3-dioxo-2H-benz[f]isoindol-2-yl)propyl]-L-leucyl-N-methyl-L-argininamide, trifluoroacetate (a) N-[(R)-1-((1,1-dimethylethoxy)carbonyl)-3-(1,3-dihydro-1,3-dioxo-2H-benz[f]isoindol-2-yl)propyl]-L-leucyl-N-methyl-N-nitro-L-argininamide (63 mg).

Prepared as described in Example 12, Step (a) using N'-nitro-N-methyl-L-argininamide (51 mg). Chemical Ionisation MS; m/e Found: 683.3 (MH+).

(b) N-[1-(R)-((1,1-Dimethylethoxy)carbonyl)-3-(1,3-dihydro-1,3-dioxo-2H-benz[f]isoindol-2-yl)propyl]-L-leucyl-N-methyl-L-argininamide A solution of the product of part (a) above (63 mg) in ethanol (10 mL) was shaken with 10% palladium on carbon (10 mg) in a hydrogen atmosphere (50 psi) at 230° for 15 h. The catalyst was removed by filtration through celite, and the solvent was evaporated to afford the title compound as a yellow oil (28 mg).

NMR (D$_2$O) δ 8.1 (s, 2H), 7.9 (m, 2H), 7.5 (m, 2H), 4.4 (t, 1H), 3.9 (t, 2H), 3.6 (m, 2H), 3.4 (t, 1H), 3.3 (t, 1H), 2.8 (m, 2H), 2.3 (s, 3H), 1.9 (m, 2), 1.4 (m, 2H), 1.3 (m, 2H), 1.2 (m, 1H), 1.1 (s, 9H), 0.6 (d, 6H).

Chemical Ionisation MS; m/e Found: 638.3 (MH+).

(c) N-[1-(R)-Carboxy-3-(1,3-dihydro-1,3-dioxo-2H-benz[f]isoindol-2-yl)propyl]-L-leucyl-N-methyl-L-argininamide, trifluoroacetate (28 mg)

Prepared as described in Example 12, Step (b) by hydrolysis of the product of part (b) above (63 mg).

NMR (CD$_3$OD) δ 8.3 (s, 2H), 8.3 (s, 2H), 8.0 (m, 2H), 7.6 (m, 2H), 7.5 (m, 2H), 4.3 (m, 1H), 3.8 (m, 2H), 3.5 (m, 2H), 3.4 (t, 1H), 3.2 (m, 1H), 3.0 (m, 2H), 2.6 (s, 3H), 2.2 (m, 2H), 1.9–1.5 (m, 5H), 0.9 (d, 6H).

High resolution MS: m/e found 582.3039 (MH+). C$_{29}$H$_{39}$N$_7$O$_6$ requires: 582.3040

EXAMPLE 21

N-[1-(R)-Carboxy-3-(1,3-dihydro-1,3-dioxo-2H-benz[f]isoindol-2-yl)propyl]-L-leucyl-N-methyl-L-tyrosinamide, trifluoroacetate (a) N-[(R)-1-((1,1-dimethylethoxy)carbonyl)-3-(1,3-dihydro-1,3-dioxo-2H-benz[f]isoindol-2-yl)propyl]-L-leucyl-N-methyl-L-tyrosinamide (60 mg)

Prepared as described in Example 12, Step (a) using L-tyrosine N-methyl amide (51 mg).

NMR (CDCl$_3$) δ 8.3 (s, 2H), 8.0 (m, 2H), 7.6 (br s, 1H), 7.5 (m, 2H), 6.7 (d, 2H), 6.3 (d, 2H), 4.2 (m, 2H), 3.4 (m, 4H), 3.1 (m, 1H), 2.6 (d, 3H), 1.8 (m, 4H), 1.4 (s, 9H), 1.2 (m, 2H), 0.9 (d, 6H).

Chemical Ionisation MS; m/e Found: 645.3 (MH+).

(b) N-[1-(R)-Carboxy-3-(1,3-dihydro-1,3-dioxo-2H-benz[f]isoindol-2-yl)propyl]-L-leucyl-N-methyl-L-tyrosinamide, trifluoroacetate (20 mg)

Prepared as described in Example 12, Step (b) by hydrolysis of the product of part (a) above (60 mg). M.p. 175°-180°.

NMR (DMSO-d6) δ 8.9 (s, 1H), 8.3 (s, 2H), 8.0 (m, 2H), 7.6 (br s, 1H), 7.5 (m, 2H), 6.7 (d, 2H), 6.3 (d, 2H), 4.2(m, 2H), 3.4 (m, 4H), 3.1 (m, 1H), 2.6 (d, 3H), 1.8(m, 4H), 1.2 (m, 2H), 0.6 (d, 6H).

High resolution MS: m/e Found 589.2652 (MH+). $C_{32}H_{36}N_4O_7$ requires: 589.2658.

EXAMPLE 22

N-[1-(R)-Carboxy-3-(1,3-dihydro-1,3-dioxo-2H-benz[f]isoindol-2-yl)propyl]-L-leucyl-N-methylglycinamide, trifluoroacetate (a) N-[(R)-1-((1,1-dimethylethoxy)carbonyl)-3-(1,3-dihydro-1,3-dioxo-2H-benz[f]isoindol-2-yl)propyl]-L-leucyl-N-methylglycinamide (27 mg)

Prepared as described in Example 12, Step (a) using N-methylglycinamide (59 mg).

Chemical Ionisation MS; m/e Found: 539.0 (MH+).

(b) N-[1-(R)-Carboxy-3-(1,3-dihydro-1,3-dioxo-2H-benz[f]isoindol-2-yl)propyl]-L-leucyl-N-methylglycinamide, trifluoroacetate (20 mg)

Prepared as described in Example 12, Step (b) by hydrolysis of the product of part (a) above (27 mg). M.p. 175°-180°.

NMR (CD$_3$OD) δ 8.3 (s, 2H), 8.0 (d, 2H), 7.8 (d, 2H), 3.9 (m, 1H), 3.85 (m, 1H), 3.8 (m, 2H), 3.7 (m, 2H), 2.5 (s, 3H), 2.3 (m, 2H), 1.8-1.7 (m, 1H), 1.7-1.6 (m, 2H), 0.9 (m, 6H).

High resolution MS: m/e found 483.2223 (MH+). $C_{25}H_{30}N_4O_6$ requires: 483.2244.

EXAMPLE 23

N-[1-(R)-Carboxy-3-(1,3-dihydro-1,3-dioxo-2H-benz[f]isoindol-2-yl)propyl]-L-leucyl-N-methyl-L-alaninamide, trifluoroacetate (a) N-[(R)-1-((1,1-Dimethylethoxy)carbonyl)-3-(1,3-dihydro-1,3-dioxo-2H-benz[f]isoindol-2-yl)propyl]-L-leucyl-N-methyl-L-alaninamide (37 mg).

Prepared as described in Example 12, Step (a) using N-methyl-L-alaninamide (40 mg).

NMR (CDCl$_3$) δ 8.4 (s, 2H), 8.2 (br s, 2H), 8.1 (m, 2H), 7.8 (m, 2H), 7.1 (m, 1H), 4.5 (m, 1H), 4.0 (m, 2H), 3.7 (t, 1H), 3.6 (t, 1H), 3.2 (br s, 1H), 2.8 (d, 3H), 2.4-2.2 (m, 2H), 1.7 (m, 2H), 1.6 (m, 1H), 1.4 (s, 9H), 1.2 (d, 3H), 0.9 (d, 6H).

Chemical Ionisation MS; m/e Found: 645.3 (MH+).

(b) N-[1-(R)-Carboxy-3-(1,3-dihydro-1,3-dioxo-2H-benz[f]isoindol-2-yl)propyl]-L-leucyl-N-methyl-L-alaninamide, trifluoroacetate (16 mg)

Prepared as described in Example 12, Step (b) by hydrolysis of the product of part (a) above (37 mg). M.p. 133°-135°.

NMR (CD3OD) δ 8.3 (s, 2H), 8.0 (dd, 2H), 7.6 (dd, 2H), 4.2 (q, 1H), 3.9 (m, 2H), 3.7 (t, 1H), 3.6 (t, 1H), 2.6 (s, 3H), 2.2 (dd, 2H), 1.7 (m, 2H), 1.5 (m, 1H), 1.3 (d, 3H), 0.9 (d, 6H).

High resolution MS: m/e found 497.2411 (MH+). $C_{26}H_{32}N_4O_6$ requires: 497.2400

EXAMPLE 24

N-[1-(R)-Carboxy-3-(1,3-dihydro-1,3-dioxo-2H-benz[f]isoindol-2-yl)propyl]-L-leucyl-N'-benzyloxymethyl-N-methyl-L-histidinamide, trifluoroacetate (a) N-[(R)-1-((1,1-Dimethylethoxy)carbonyl)-3-(1,3-dihydro-1,3-dioxo-2H-benz[f]isoindol-2-yl)propyl]-L-leucyl-N'-benzyloxymethyl-N-methyl-L-histidinamide (63 mg)

Prepared as described in Example 12, Step (a) using N'-benzyloxymethyl-N-methyl-L-histidinamide (51 mg).

NMR (CDCl$_3$) δ 9.0 (m, 1H), 8.4 (s, 1H), 8.2 (s, 2H), 8.0 (m, 2H), 7.7 (m, 2H), 7.6-7.4 (m, 3H), 7.3 (m, 5H), 5.6 (m, 2H), 4.6 (m, 2H), 2.5 (d, 3H), 2.2 (m, 2H), 1.6 (m, 2H), 1.4 (m, 1H), 1.3 (s, 9H), 0.9 (d, 6H).

Chemical Ionisation MS; m/e Found: 739.3 (MH+).

(b) N-[1-(R)-Carboxy-3-(1,3-dihydro-1,3-dioxo-2H-benz[f]isoindol-2-yl)propyl]-L-leucyl-N'-benzyloxymethyl-N-methyl-L-histidinamide, trifluoroacetate (20 mg)

Prepared as described in Example 12, Step (b) by hydrolysis of the product of part (a) above (67 mg). M.p. 130°-135°.

NMR (CDCl$_3$) δ 8.9 (m, 1H), 8.3 (s, 1H), 8.2 (s, 2H), 8.0 (m, 2H), 7.6 (m, 2H), 7.2 (m, 5H), 5.7 (m, 2H), 4.6 (m, 2H), 4.2 (m, 2H), 3.7 (m, 1H), 3.4 (m, 2H), 3.0 (m, 1H), 2.5 (s, 3H), 2.2 (m, 2H), 1.6 (m, 2H), 1.4 (m, 1H), 0.9 (d, 6H).

High resolution MS: m/e Found 683.3195 (MH+). $C_{37}H_{43}N_6O_7$ requires: 683.3193.

EXAMPLE 25

N-[1-(R)-Carboxy-3-(1,3-dihydro-1,3-dioxo-2H-benz[f]isoindol-2-yl)propyl]-L-leucyl-N-methyl-L-histidinamide, trifluoroacetate A solution of the product of Example 24, Step (a) (40 mg) in hydrofluoric acid (3 mL) was stirred at 0° for 0.5 h. The solvent was evaporated and the residue purified by reverse phase HPLC to afford the title compound as a white solid (0.9 mg). M.p. 165°-170°. NMR (CD$_3$OD) δ 8.7 (m, 1H), 8.3 (s, 2H), 8.0 (m, 2H), 7.9 (m, 2H), 7.6 (dd, 2H), 4.6 (t, 1H), 3.8 (m, 2H), 3.6 (t, 1H), 3.5 (t, 1H), 3.2 (d, 2H), 2.5 (s, 3H), 2.2 (m, 2H), 1.6 (m, 3H), 0.9 (d, 6H).

High resolution MS: m/e Found 563.2615 (MH+). $C_{29}H_{35}N_6O_6$ requires: 563.2617.

EXAMPLE 26

N-[1-(R)-Carboxy-3-(1,3-dihydro-1,3-dioxo-2H-benz[f]isoindol-2-yl)propyl]-L-leucyl-L-phenylalanylglycine trifluoroacetate (a) N-[(R)-1-((1,1-Dimethylethoxy)carbonyl)-3-(1,3-dihydro-1,3-dioxo-2H-benz[f]isoindol-2-yl)propyl]-L-leucyl-L-phenylalanylglycine t-butyl ester (150 mg)

Prepared as described in Example 12, Step (a) using L-phenylalanylglycine t-butyl ester (170 mg).

NMR (CDCl$_3$) δ 8.33 (2H, s), 8.05 (2H, m), 7.70 (3H, m), 7.30–7.10 (6H, m), 4.75 (1H, m), 4.20 (1H, m), 3.95 (1H, m), 3.75 (1H, m), 3.50 (1H, m), 3.35 (2H, m), 3.05 (2H, m), 1.95 (2H, m), 1.70–1.05 (6H, m), 1.25 (18H, s), 0.82 (6H, m).

(b) N-[1-(R)-Carboxy-3-(1,3-dihydro-1,3-dioxo-2H-benz[f]isoindol-2-yl)propyl]-L-leucyl-L-phenylalanylglycine trifluoroacetate (52 mg)

Prepared as described in Example 12, Step (b) by hydrolysis of the product of part (a) above (140 mg). M.p. 205°–207° (d).

NMR (DMSO-d6) δ 8.54 (2H, s), 8.30 (2H, m), 7.85 (2H, m), 7.30–7.10 (7H, m), 4.70 (1H, br m), 3.80 (2H, m), 3.10 (m), 2.80 (m), 1.95 (m), 1.65 (m), 1.30 (m), 0.85 (6H, m).

High resolution MS: m/e Found 617.2601 (MH+). $C_{33}H_{36}N_4O_8$ requires: 617.2611.

EXAMPLE 27

N-[1-(R)-Carboxy-3-(1,3-dihydro-1,3-dioxo-2H-benz[f]isoindol-2-yl)propyl]-L-leucyl-N-methyl-L-phenylglycinamide, trifluoroacetate (a) N-[(R)-1-((1,1-Dimethylethoxy)carbonyl)-3-(1,3-dihydro-1,3-dioxo-2H-benz[f]isoindol-2-yl)propyl]-L-leucyl-N-methyl-L-phenylglycinamide (27 mg)

Prepared as described in Example 12, Step (a) using N-methyl-L-phenylglycinamide (15 mg).

(b) N-[1-(R)-Carboxy-3-(1,3-dihydro-1,3-dioxo-2H-benz[f]isoindol-2-yl)propyl]-L-lencyl-N-methyl-L-phenylglycinamide,trifluoracetate (19 mg)

Prepared as described in Example 12, Step (b) by hydrolysis of the product of part (a) above (27 mg).

NMR (DMSO-d6) δ 8.52(s, 2H), 8.22 (2H, m), 7.79 (2H, m), 7.16–7.42 (5H, m), 5.40 (1H, d), 3.20–3.80 (m, obscured by water), 2.56 (3H, d), 2.10 (m), 1.40–1,70 (3H, m), 0.89 (6H, m).

High resolution MS:m/e Found 559.2552 (MH+). $C_{31}H_{35}N_4O_6$ requires: 559.2557.

EXAMPLE 28

N-[1-(R)-Carboxy-3-(1,3-dihydro-1,3-dioxo-2H-benz[f]isoindol-2-yl)propyl]-L-leucyl-N-(morpholinoethyl)-L-phenylalaninamide, ditrifluoroacetate (a) N-[(R)-1-[(1,1-Dimethylethoxy)carbonyl]-3-(1,3-dihydro-1,3-dioxo-2H-benz[f]isoindol-2-yl)propyl]-L-leucyl-N-(morpholinoethyl)-L-phenylalaninamide (210 mg)

Prepared as described in Example 12, Step (a) using N-(morpholinoethyl)-L-phenylalaninamide (138 mg).

(b) N-[1-(R)-Carboxy-3-(1,3-dihydro-1,3-dioxo-2H-benz[f]isoindol-2-yl)propyl]-L-leucyl-N-(morpholinoethyl)-L-phenylalaninamide, ditrifluoroacetate (144 mg)

Prepared as described in Example 12, Step (b) by hydrolysis of the product of part (a) above (210 mg).

NMR (CD$_3$OD) δ 8.37 (2H, s), 8.11 (2H, dd), 7.73 (2H, dd), 7.16–7.25 (5H, m), 4.62 (1H, t), 3.00–4.00 (m), 2.18 (2H, q), 1.58–1.81 (3H, m), 0.95 (6H, m).

High resolution MS:m/e Found 672.3420 (MH+). $C_{37}H_{46}N_5O_7$ requires 672.3397.

EXAMPLE 29

N-[1-(R,S)-[Ethoxycarbonyl]-3-(1,3-dihydro-1,3-dioxo-2H-isoindol-2-yl)propyl]-L-leucyl-N-methyl-L-phenylalaninamide A mixture of Intermediate 51 (73 mg) and Intermediate 52 (65 mg) in 1,2-dichloroethane (5 mL) was treated with acetic acid (50 mg) and stirred at 23° for 2 h. The mixture was treated with sodium triacetoxyborohydride (90 mg) was added and the mixture stirred at 23° for 15 h. Water (20 mL) was added and the mixture extracted with methylene chloride (2×10 mL). The combined organic layers were dried (Na$_2$SO$_4$) and evaporated. Purification by chromatography using 50% ethyl acetate-hexane as eluent afforded the title compound (32 mg) as a mixture of diastereoisomers.

NMR (CDCl$_3$) δ 7.84 (2H, m), 7.74 (3H, m), 7.25 (5H, m), 6.92 (1H, m), 6.38 (1H, m), 6.27 (1H, m), 4.72 (1H, m), 4.58 (1H, m), 4.15–3.85 (4H, m), 3.75 (4H, m), 3.20–3.00 (3H, m), 2.70 (3H, m), 2.25 (2H, q), 2.00 (2H, m), 1.80–1.40 (8H, m), 1.24 (t, J=7.0 Hz), 1.18 (t, J=7.2 Hz), 0.92 (d, J=6.6 Hz), 0.85 (d, J=6.6 Hz).

EXAMPLE 30

N-[1-(R)-Carboxy-3-(1,3-dihydro-1,3-dioxo-5-phenyl-2-yl)propyl]-L-leucyl-N-methyl-L-phenylalaninamide (a) N-[1-(R)-[(1,1-Dimethylethoxy)carbonyl]-3-(1,3-dihydro-1,3-dioxo-5-phenyl-2H-isoindol-2-yl)propyl]-L-leucyl-N-methyl-L-phenylalaninamide (120 mg)

Prepared as described in Example 1, Step (a) using 2,3-dihydro-5-phenyl-1H-isoindol-1,3-(2H)-dione (100 mg).

NMR (CDCl$_3$) δ 8.03 (2H, m), 7.88 (1H, d), 7.64 (2H, m), 7.44 (3H, m), 7.14 (5H, m), 4.65 (1H, m), 3.70 (2H, m), 3.57 (1H, m), 3.46 (1H, m), 2.98 (2H, m), 2.57 (3H, s), 1.95 (2H, m), 1.65 (3H, m), 1.48 (9H, s), 0.88 (6H, dd).

(b) N-[1-(R)-Carboxy-3-(1,3-dihydro-1,3-dioxo-5-phenyl-2H-isoindol-2-yl)propyl]-L-leucyl-N-methyl-L-phenylalaninamide (72 mg)

Prepared as described in Example 1, Step (b) using the product of part (a) above. M.p. 83°–100°.

NMR (CD$_3$OD) δ 7.96 (2H, m), 7.81 (1H, d), 7.55 (2H, m), 7.38 (3H, m), 7.10 (5H, m), 4.57 (1H, m), 3.72 (1H, m), 3.60 (3H, m), 2.85 (2H, m), 2.49 (3H, s), 1.95 (2H, m), 1.53 (3H, m), 0.85 (6H, dd).

High resolution mass spectrometry: m/e found: 599.2 (MH+).

EXAMPLE 31

N-[1-(R)-Carboxy-3-(1,3-dihydro-5,6-dimethyl-1,3-dioxo-2H-isoindol-2-yl)propyl]-L-leucyl-N-methyl-L-phenylalaninamide (a) N-[1-(R)-[(1,1-Dimethylethoxy)carbonyl]-3-(1,3-dihydro-5,6-dimethyl-1,3-dioxo-2H-isoindol-2-yl)propyl]-L-leucyl-N-methyl-L-phenylalaninamide (33 mg)

Prepared as described in Example 1, Step (a) using 2,3-dihydro-5,6-dimethyl-1H-isoindol-1,3-(2H)-dione (25 mg).

NMR (CDCl$_3$) δ 7.60 (2H, s), 7.10 (5H, s), 4.80 (1H, m), 3.90–3.70 (4H, m), 3.50 (1H, m), 3.30 (1H, dd), 3.10

(1H, dd), 2.80 (3H, d), 2.20 (2H, m), 1.50 (1H, m), 1.40 (9H, s), 0.90 (6H, m).

(b) N-[1-(R)-Carboxy-3-(1,3-dihydro-5,6-dimethyl-1,3-dioxo-2H-isoindol-2-yl)propyl]-L-leucyl-N-methyl-L-phenylalaninamide (18 mg)

Prepared as described in Example 1, Step (b) using the product of part (a) above. M.p. 140°-2°.

NMR (CD₃OD) δ 7.50 (2H, s), 7.10 (5H, m), 4.50 (1H, m), 3.60 (3H, m), 3.40 (1H, m), 3.00 (1H, dd), 2.90 (1H, dd), 2.50 (3H, s), 2.20 (6H, s), 1.90 (2H, m), 1.60-1.40 (3H, m), 0.90 (6H, m).

High Resolution mass spectrometry: m/e found: 551.2871 (MH+); $C_{30}H_{39}N_4O_6$ Requires 551.2868.

EXAMPLE 32

N-[1(R)-Carboxy-3-(6,8-dihydro-6,8-dioxo-7H-1,4-dioxino[2,3-f]isoindol-7-yl)propyl]-L-lecuyl-N-methyl-L-phenylalaninamide (a) N-[1-(R)-[(1,1-Dimethylethoxy)carbonyl]-3-(6,8-dihydro-6,8-dioxo-7H, -1,4-dioxino[2,3-]isoindol-7-yl)propyl]-L-leucyl-N-methyl-L-phenylalaninamide (56 mg)

Prepared as described in Example 1, Step (a) using Intermediate 53 (70 mg). NMR (CD₃OD) δ7.23 (2H, s), 7.15 (5H, m), 4.61 (1H, m), 4.27 (4H, s), 3.50-3.59 (4, m), 3.00 (2H, m), 2.57(3H, s), 1.88(3H, m), 1.58(2H, m), 1.42(9H, s), 0.85 (6H, dd).

(b)

N-[1-(R)-Carboxy-3-(6,8-dihydro-6,8-dioxo-7H-1,4-dioxino[2,3-f]isoindol-7yl)propyl]-L-leucyl-N-methyl-L-phenylalaninamide (7.8 mg)

Prepared as described in Example 1, Step (b) using the product of part (a) above. M.p. 214°-7°.

NMR (CD₃OD) δ 7.21 (2H, s), 7.18 (5H, m), 4.53 (1H, m), 4.24 (4H, s), 3.42-3.60(4H, m), 2.90(2H, m), 2.52(3H, s), 1.86(2H, m), 1.41-1.5 (3H, m), 0.86(1H, dd).

High Resolution mass spectrometry: m/e found 581.2584 (MH+); $C_{30}H_{37}N_4O_8$ Requires 581.2610.

EXAMPLE 33

N-[1-(R)-Carboxy-3-(5,7-dihydro-5,7-dioxo-6-H-1,3-dioxolo[4,5-f]isoindol-6-yl)propyl]-L-leucyl-N-methyl-L-phenylalaninamide (a) N-[1-(R)-](1,1-Dimethylethoxy)carbonyl]-3(5,7-dihydro-5,7-dioxo-6H-1,3-dioxolo[4,5-f]isoindol6-yl)-propyl]-L-leucyl-N-methyl-L-phenylalaninamide (48 mg).

Prepared as described in Example 1, Step (a) using 5H-1,3-dioxolo[4,5-f]isoindole-5,7(6H)-dione (80 mg).

NMR (CD₃OD) δ 7.17 (7H, m), 6.09 (2H, s), 4.69 (1H, m), 3.67 (1H, m), 3.57 (1H, m), 3.40 (2H, m), 2.95 (2H, m), 2.55 (3H, s), 1.90 (2H, m), 1.50-1.77 (3H, m), 1.44 (9H, s), 0.88 (6H, dd).

(b) N-[1-(R)-Carboxy-3-(5,7-dihydro-5,7-dioxo-6H-1,3-dioxolo[4,5-f]isoindol-6-yl)propyl]-L-leucyl-N-methyl-L-phenylalaninamide (7 mg).

Prepared as described in Example 1, Step (b) using the product of Step (a) above. M.p. 100°-110°.

NMR (CD₃OD) δ 7.26 (7H, m), 6.19 (2H, s), 4.68 (1H, m), 3.86 (1H, m), 3.66 (3H, m), 2.96 (2H, m), 2.64 (3H, s), 2.03 (2H, m), 1.62-1.80 (3H, m), 0.95 (6H, dd).

EXAMPLE 34

N-[1-(R)-Carboxy-3-(1,3-dihydro-1,3-dioxo-5-propyloxy-2H-isoindol-2-yl)propyl]-L-leucyl-N-methyl-L-phenylalaninamide (a) N-[1-(R)-[(1,1-Dimethylethoxy)carbonyl]-3-(1,3-dihydro-1,3-dioxo-5-propyloxy-2H-isoindol-2-yl)propyl]-L-leucyl-N-methyl-L-phenylalaninamide (190 mg).

Prepared as described in Example 1, Step (a) using 1,3-dihydro-1,3-dioxo-5-propyloxy-2H-isoindole (92 mg).

NMR (CDCl₃) δ 8.26 (1H, br d, J=8.5 Hz), 7.71 (1H, d, J=8.3 Hz), 7.29 (1H, d, J=2 Hz), 7.24-7.12 (5H, m), 6.00 (2H, br), 4.80 (1H, m), 4.02 (2H, t, J=6.6 Hz), 3.80-3.60 (3H, m), 3.48 (1H, t, J=5.5 Hz), 3.24 (1H, A part of ABX system, dd, Jab=1.04 Hz, Jax=5.7 Hz), 3.02 (1H, B part of ABX system, dd, Jab=14.0 Hz, Jbx=9.2 Hz), 2.74 (3H, d, J=4.4 Hz), 2.20 (2H, m), 1.86 (2H, m), 1.70-1.45 (3H, m), 1.38 (9H, s), 1.05 (3H, t, J=7.3 Hz), 0.85 (6H, t, J=6.0 Hz).

(b) N-[1-(R)-Carboxy-3-(1,3-dihydro-1,3-dioxo-5-propyloxy-2H-isoindol-2-yl)propyl]-L-leucyl-N-methyl-L-phenylalaninamide (55 mg)

Prepared as described in Example 1, Step (b) using the product of Step (a) above. M.p. 91°-101°.

NMR (CD₃OD) δ 7.88 (1H, br m), 7.67 (1H, d, J=8.3 Hz), 7.25 (1H, d, J=2.2 Hz), 7.20-7.05 (6H, m), 4.56 (1H, dd, J=6.6 Hz, J'=8.8 Hz), 3.97 (2H, t, J=6.3 Hz), 3.70-3.56 (3H, m), 3.52 (1H, dd, J=5.1 Hz, J'=6.6 Hz), 3.20 (1H, quin, J=1.6 Hz), 3.01 (1H, A part of ABX system, Jab=13.8 Hz, Jax=6.7 Hz), 2.86 (1H, B part of ABX system, Jab=13.7 Hz, Jbx=9.0 Hz), 2.55 (3H, s), 1.95 (2H, m), 1.76 (2H, hex, J=6.9 Hz), 1.65-1.45 (3H, m), 0.96 (3H, t, J=7.4 Hz), 0.87 (3H, d, J=5.8 Hz), 0.83 (3H, d, J=5.8 Hz).

High Resolution mass spectrometry: m/e found 581.2979 (MH+); $C_{31}H_{41}N_4O_7$ Requires 581.2975.

We claim:

1. A compound of general formula (I)

$$\text{HetCH}_2\text{CH}_2\overset{CO_2H}{\underset{}{\text{CHNHCHCONHCHCONHR}^3}}\overset{R^1}{\underset{R^2}{}}\quad (I)$$

wherein:
$R^1$ is $C_{3-6}$alkyl or $C_{1-3}$alkylthio$C_{1-3}$alkyl;
$R^2$ is an optionally substituted $C_{1-6}$alkyl or $C_{1-6}$alkoxy group, aryl, heteroaryl, aryl$C_{1-4}$alkyl, heteroaryl$C_{1-4}$alkyl or a side-chain of a natural α-amino acid;
$R^3$ is hydrogen, $C_{1-6}$alkyl, CHR⁴COR⁵ (where $R^4$ is a side-chain of a natural α-amino acid and $R^5$ is hydroxyl, $C_{1-6}$alkoxy or NHR⁶ where $R^6$ represents a hydrogen atom or a $C_{1-6}$alkyl group) or a group (CH₂)ₙX (where n is 1 to 6 and X is hydroxyl, $C_{1-4}$alkoxy, heteroaryl or a group NR⁷R⁸ where $R^7$ and $R^8$ are each hydrogen or $C_{1-6}$alkyl or the group NR⁷R⁸ forms a 5 to 7 membered cyclic amine); and Het is an optionally substituted cyclic imide where the cyclic imide ring system has the formula (i), (ii) or (iii)

(i)

[structure i]

(ii)

[structure ii]

(iii)

[structure iii]

in which A, B, C and D are each CH and E and F each represent CH and where the optional substituents in formula (i) are a halogen atom or a group selected from hydroxyl, $C_{1-6}$alkyl (e.g. t-butyl), nitro, $C_{1-6}$alkoxy, $R^{11}CONH(CH_2)_m-$, $R^{12}NHCO(CH_2)_m-$,

[O N(CH₂)ₘ— or R¹³N N(CH₂)ₘ—]

(where m is zero, 1, 2 or 3, $R^{11}$ is $C_{1-6}$alkyl, $R^{12}$ is hydrogen or $C_{1-6}$alkyl and $R^{13}$ is hydrogen or $C_{1-3}$alkyl) and the optional substituents in formula (ii) or formula (iii) are a halogen atom or a group selected from hydroxyl, $C_{1-3}$ alkyl and $C_{1-3}$ alkoxy; and physiologically acceptable salts and solvates thereof.

2. A compound according to claim 1 in which $R^1$ represents $C_{3-6}$ alkyl.

3. A compound according to claim 2 in which $R^1$ represents isobutyl.

4. A compound according to claim 1 in which $R^2$ represents $C_{1-6}$ alkyl, aryl, arylmethyl or heteroarylmethyl.

5. A compound according to claim 1 in which $R^3$ represents $C_{1-3}$ alkyl or $(CH_2)nX$ where n is 1–3 and X is a group $NR^7R^8$ where $NR^7R^8$ forms a 5 or 6 membered cyclic amine.

6. A compound according to claim 1 in which Het represents an optionally substituted 2,3-dihydro-1,3-dioxo-1H-isoindol-2-yl group.

7. A compound according to claim 1 in which Het represents the ring

[structure]

which may be optionally substituted.

8. A compound according to claim 7 in which Het represents a 1,3-dihydro-1,3-dioxo-2H-benz[f]isoindol-2-yl group optionally substituted by a $C_{1-3}$ alkoxy group.

9. N-[1-(R)-Carboxy-3-(1,3-dihydro-1,3-dioxo-2H-benz[f]isoindol-2-yl)propyl]-L-leucyl-N-methyl-L-phenylalaninamide, N-[1-(R)-carboxy-3-(1,3-dihydro-4-methoxy-1,3-dioxo-2H-benz[f]isoindol-2-yl)propyl]-L-leucyl-N-methyl-L-phenylalaninamide, N-[1-(R)-carboxy-3-(1,3-dihydro-5-methoxy-1,3-dioxo-2H-benz[f]isoindol-2-yl)propyl]-L-leucyl-N-methyl-L-phenylalaninamide, N-[1-(R)-Carboxy-3-(1,3-dihydro-1,3-dioxo-2H-benz[f]isoindol-2-yl)propyl]-L-leucyl-N-(morpholinoethyl)-L-leucinamide, N-[1-(R)-carboxy-3-(1,3-dihydro-1,3-dioxo-2H-benz[f]isoindol-2-yl)propyl]-L-leucyl-N-methyl-L-tyrosinamide, N-[1-(R)-carboxy-3-(1,3-dihydro-1,3-dioxo-2H-benz[f]isoindol-2yl)propyl]-L-leucyl-N-methyl-L-phenylglycinamide, N-[1-(R)-carboxy-3-(1,3-dihydro-1,3-dioxo-2H-benz[f]isoindol-2-yl)propyl]-L-leucyl-N-(morpholinoethyl)-L-phenylalaninamide, and physiologically acceptable salts and solvents thereof.

10. A pharmaceutical formulation comprising a compound as claimed in claim 1 together with one or more pharmaceutically acceptable carriers or excipients.

11. A method for the treatment of diseases involving tissue degradation which comprises administering to an animal subject an effective amount of a compound according to claim 1.

* * * * *